(12) United States Patent
Pallerla et al.

(10) Patent No.: US 11,176,391 B1
(45) Date of Patent: Nov. 16, 2021

(54) TEMPERATURE MEASUREMENT VIA ULTRASONIC SENSOR

(71) Applicant: QUALCOMM Incorporated, San Diego, CA (US)

(72) Inventors: Rakesh Pallerla, Hyderabad (IN); Naga Chandan Babu Gudivada, Hyderabad (IN); Javier Frydman, Tel-Mond (IL)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/247,998

(22) Filed: Jan. 4, 2021

(51) Int. Cl.
*G06K 9/00* (2006.01)

(52) U.S. Cl.
CPC ..... *G06K 9/00892* (2013.01); *G06K 9/00912* (2013.01); *G06K 9/0002* (2013.01)

(58) Field of Classification Search
CPC .......... G06K 9/00892; G06K 9/00912; G06K 9/0002; G06K 9/00342; G06K 2009/00939; G06K 9/00885; G06K 2009/00932; G06K 7/10009; G06K 7/10792; G06K 9/00496; G06K 9/00771; G06K 9/2018; G06K 9/6277; G06K 19/06037; G06K 2007/10524; G06K 2009/00953; G06K 7/10297; G06K 9/00013; G06K 9/0008; G06K 9/00221; G06K 9/00362; G06K 9/209; G06K 9/6267; G06K 9/00315; G06K 9/6292; G06K 9/0061; G06K 9/00617; G06K 9/3216; G06K 9/00087; G06K 9/001; G06K 9/00107; G06K 9/00906; G06K 9/00006; G06K 9/00993; G06K 2009/00583; G06K 9/0004; G06K 9/00899; G06K 2009/00738; G06K 9/00711; G06K 9/00724; G06K 9/00751; G06K 9/00832; G06K 9/00845; G06K 9/78; H04L 67/22; H04L 67/10; H04L 67/306; H04L 63/10; H04L 9/3231; H04L 63/0861; H04L 63/0492; H04L 63/0853; H04L 63/107;
(Continued)

(56) References Cited

U.S. PATENT DOCUMENTS

2018/0204040 A1* 7/2018 Kwon ................... G06F 3/0421
2019/0354210 A1* 11/2019 Akhbari ............... G06F 3/0436
(Continued)

*Primary Examiner* — Nimesh Patel
(74) *Attorney, Agent, or Firm* — QUALCOMM Incorporated

(57) ABSTRACT

Some disclosed methods involve acquiring first ultrasonic signals corresponding to reflections from a cover/air interface of an apparatus that includes an ultrasonic sensor system, and determining one or more first ultrasonic signal parameters of the first ultrasonic signals. Some methods involve acquiring second ultrasonic signals corresponding to reflections from a cover/target interface, and determining one or more second ultrasonic signal parameters of the second ultrasonic signals. Some methods involve estimating, based at least in part on the one or more first ultrasonic signal parameters, the one or more second ultrasonic signal parameters and the ultrasonic sensor system temperature, a target object temperature. Some disclosed methods involve receiving ultrasonic sensor system temperature data indicating a temperature of an ultrasonic sensor system and calibrating the ultrasonic sensor system according to the temperature.

38 Claims, 17 Drawing Sheets

(58) Field of Classification Search
CPC ....... H04L 67/42; H04L 9/0866; H04L 63/20;
H04L 63/105; H04W 12/06; H04W
12/08; H04W 4/38; H04W 4/21; H04W
12/065; H04W 52/0254; H04W 12/37;
H04W 12/68; H04W 12/062; H04W
84/22; H04W 4/025; H04W 8/22; H04W
12/69; H04W 4/023; H04W 64/006;
H04W 4/02; H04W 4/027; H04W 4/90;
G06F 3/0481; G06F 15/16; G06F 21/32;
G06F 21/6245; G06F 21/31; G06F 3/017;
G06F 21/62; G06F 21/316; G06F 3/011;
G06F 21/445; G06F 21/53; G06F 21/57;
G06F 2221/2129; G06F 2221/2149; G06F
2203/011; G06F 2203/04104; G06F
2221/2113; G06F 3/013; G06F 3/04186;
G06F 3/0488; G06F 21/00; G06F 3/0484;
G06F 16/436; G06F 21/86; G06F
2221/2133; G06F 1/163; G06F 1/203;
G06F 1/206; G06F 3/0436; G06F
2221/2117; G06F 16/29; G06F 21/36;
G06F 21/321; G06F 1/3231; G06N 7/005;
G06N 5/022; G06N 20/00; G06N 5/003;
G06N 5/02; G06N 5/04; G06N 3/004;
G06N 3/08; G07C 9/26; G07C 9/37;
G07C 9/00309; G07C 9/0069; G07C
9/25; G07C 9/27; G07C 9/29; G07C
9/38; G07C 9/28; G07C 9/32; G05B
15/02; G05B 13/028; G05B 13/048;
G06Q 10/063114; G06Q 20/327; G06Q
20/40; G06Q 10/02; G06Q 20/4016;
G06T 2207/30221; G06T 7/20; G06T
2207/10016; G06T 2207/10004; G06T
2207/20076; G06T 2207/20081; G06T
2207/30241; G06T 7/11; G06T 2207/30;
G08B 21/0492; G08B 25/016; G08B
21/0453; G08B 13/19621; G08B 21/02;
G08B 21/0423; G08B 21/0446; G08B
21/0461; H04M 2250/12; H04M 1/72454;
H04M 1/72412; H04M 15/93; H04M
1/72463; H04M 1/72418; H04M 3/5116
See application file for complete search history.

(56) References Cited

U.S. PATENT DOCUMENTS

| | | | |
|---|---|---|---|
| 2020/0074134 A1* | 3/2020 | Lim | G06K 9/0002 |
| 2020/0175291 A1* | 6/2020 | Kitchens | G06K 9/0002 |
| 2020/0257873 A1* | 8/2020 | Heo | H01L 27/1214 |

* cited by examiner

405

| Temp | LUT | | |
|---|---|---|---|
| | Frequency | RGD | Dbias |
| -20 | 18.14478375 | 0.480301 | 5.9765 |
| -15 | 17.95336 | 0.511139 | 5.868 |
| -10 | 17.76410375 | 0.539589 | 5.7595 |
| -5 | 17.577015 | 0.565651 | 5.651 |
| 0 | 17.39209375 | 0.589325 | 5.5425 |
| 5 | 17.20934 | 0.610611 | 5.434 |
| 10 | 17.02875375 | 0.629509 | 5.3255 |
| 15 | 16.850335 | 0.646019 | 5.217 |
| 20 | 16.67408375 | 0.660141 | 5.1085 |
| 25 | 16.5 | 0.671875 | 5 |
| 30 | 16.32808375 | 0.681221 | 4.8915 |
| 35 | 16.158335 | 0.688179 | 4.783 |
| 40 | 15.99075375 | 0.692749 | 4.6745 |
| 45 | 15.82534 | 0.694931 | 4.566 |
| 50 | 15.66209375 | 0.694725 | 4.4575 |
| 55 | 15.501015 | 0.692131 | 4.349 |

*Figure 4*

TEMPERATURE MEASUREMENT VIA ULTRASONIC SENSOR

TECHNICAL FIELD

This disclosure relates generally to sensor devices and related methods, including but not limited to ultrasonic sensor systems and methods for using such systems.

DESCRIPTION OF THE RELATED TECHNOLOGY

Biometric authentication can be an important feature for controlling access to devices, etc. Many existing products include some type of biometric authentication. Although some existing biometric authentication technologies provide satisfactory performance under some conditions, improved methods and devices would be desirable.

SUMMARY

The systems, methods and devices of the disclosure each have several innovative aspects, no single one of which is solely responsible for the desirable attributes disclosed herein.

One innovative aspect of the subject matter described in this disclosure may be implemented in an apparatus. The apparatus may include an ultrasonic sensor system, a control system and a cover. In some examples, the ultrasonic sensor system may include a piezoelectric layer, an ultrasonic sensor system electrode proximate a first side of the piezoelectric layer and an array of ultrasonic sensor pixels proximate a second side of the piezoelectric layer. In some implementations, the apparatus may include a temperature sensor configured to determine an ultrasonic sensor system temperature. In some examples, the apparatus may be integrated into a mobile device.

In some examples, at least part the control system is coupled (e.g. electrically or wirelessly coupled) to the ultrasonic sensor system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

According to some examples, the control system may be configured to receive ultrasonic sensor system temperature data from the temperature sensor. In some instances, the ultrasonic sensor system temperature data may indicate the ultrasonic sensor system temperature. In some examples, the control system may be configured to acquire first ultrasonic signals via the ultrasonic sensor system. The first ultrasonic signals may be received by the ultrasonic sensor system electrode and may correspond to reflections from a cover/air interface. According to some examples, the control system may be configured to determine one or more first ultrasonic signal parameters of the first ultrasonic signals.

In some examples, the control system may be configured to acquire second ultrasonic signals from a target proximate the cover via the ultrasonic sensor system. The second ultrasonic signals may, in some instances, be received by the ultrasonic sensor system electrode and may correspond to reflections from a cover/target interface. According to some examples, the control system may be configured to determine one or more second ultrasonic signal parameters of the second ultrasonic signals. In some examples, the control system may be configured to estimate, based at least in part on the one or more first ultrasonic signal parameters, the one or more second ultrasonic signal parameters, and the ultrasonic sensor system temperature, a target object temperature of the target object.

In some implementations, the apparatus may include a memory. In some such implementations, the control system may be further configured to retrieve previously-acquired ultrasonic signal parameter data and previously-acquired temperature data from the memory and to estimate the target object temperature based, at least in part, on the previously-acquired ultrasonic signal parameter data and the previously-acquired temperature data.

In some examples, the target object may be a body part of a user of the apparatus. In some such examples, the previously-acquired ultrasonic signal parameter data and the previously-acquired temperature data may have been previously acquired from the user (e.g., via the control system) during a user calibration stage.

In some implementations, the apparatus may include a user interface system. The control system may, in some such examples, be further configured to control the user interface system to provide one or more user prompts. In some examples, the user interface system may include a display stack. According to some examples, the cover may be, or may include, a cover glass. At least a portion of the display stack may reside between the cover glass and the ultrasonic sensor system. However, in some instances some or all of the cover may be optically opaque.

In some implementations, the control system may be further configured for controlling the display stack to present a graphical user interface that indicates an ultrasonic sensor system area. According to some implementations, the control system may be configured for controlling the display stack to present text prompting the user to ensure that there is no object on or proximate the ultrasonic sensor system area prior to acquiring ultrasonic signals corresponding to reflections from the cover/air interface during the user calibration stage, prior to acquiring the first ultrasonic signals, or both during the user calibration stage and prior to acquiring the first ultrasonic signals. In some examples, the control system may be configured for controlling the display stack to present text prompting the user to position the body part on the ultrasonic sensor system area prior to acquiring ultrasonic signals corresponding to reflections from a cover/body part interface during the user calibration stage, prior to acquiring the second ultrasonic signals, or both during the user calibration stage and prior to acquiring the second ultrasonic signals. According to some examples, the control system may be further configured for controlling the display stack to present a graphical user interface that indicates an estimated body temperature of the user.

In some instances, the previously-acquired ultrasonic signal parameter data and the previously-acquired temperature data may not have been previously acquired from a body part of a user. In some such examples, the previously-acquired ultrasonic signal parameter data and the previously-acquired temperature data may have been acquired from a plurality of persons. In some instances, the previously-acquired ultrasonic signal parameter data and the previously-acquired temperature data may have been acquired via a plurality of devices.

According to some examples, the one or more first ultrasonic signal parameters and the one or more second ultrasonic signal parameters may include frequency, amplitude, phase and/or decay coefficient. In some instances, acquiring the first ultrasonic signals and the second ultrasonic signals involves controlling the ultrasonic sensor system to transmit ultrasonic waves according to each of a plurality of modes. According to some examples, each of the modes may correspond with a different combination of ultrasonic sensor system parameters.

In some examples, the control system may be configured to perform an authentication process that is based, at least in part, on ultrasonic signals received via the array of ultrasonic sensor pixels. According to some examples, the control system may be configured to cause the piezoelectric layer to transmit ultrasonic waves by applying a voltage to the ultrasonic sensor system electrode. In some examples, the second ultrasonic signals also may correspond to reflections from within the target object.

Other innovative aspects of the subject matter described in this disclosure may be implemented in a method. In some examples, the method may involve receiving ultrasonic sensor system temperature data from a temperature sensor configured to determine an ultrasonic sensor system temperature of an ultrasonic sensor system. The ultrasonic sensor system temperature data may, for example, indicate the ultrasonic sensor system temperature. In some examples, the method may involve acquiring first ultrasonic signals via the ultrasonic sensor system. In some instances, the first ultrasonic signals may correspond to reflections from a cover/air interface. The cover/air interface may be an interface between air and a cover of an apparatus that includes the ultrasonic sensor system.

In some examples, the method may involve determining one or more first ultrasonic signal parameters of the first ultrasonic signals. In some examples, the method may involve acquiring second ultrasonic signals from a target proximate the cover via the ultrasonic sensor system. The second ultrasonic signals may, in some instances, be received by an ultrasonic sensor system electrode and may correspond to reflections from a cover/target interface. In some examples, the method may involve determining one or more second ultrasonic signal parameters of the second ultrasonic signals. In some examples, the method may involve estimating, based at least in part on the one or more first ultrasonic signal parameters, the one or more second ultrasonic signal parameters, and the ultrasonic sensor system temperature, a target object temperature of the target object. According to some examples, the method may involve controlling a display to present a graphical user interface that indicates an estimated target object temperature.

According to some examples, the method may involve retrieving previously-acquired ultrasonic signal parameter data and previously-acquired temperature data from a memory and estimating the target object temperature based, at least in part, on the previously-acquired ultrasonic signal parameter data and the previously-acquired temperature data.

In some examples, the target object may be a body part of a user of the apparatus. In some examples, the previously-acquired ultrasonic signal parameter data and the previously-acquired temperature data may have been previously acquired from the user during a user calibration stage.

According to some examples, the ultrasonic sensor system may include a piezoelectric layer. The ultrasonic sensor system electrode may be proximate a first side of the piezoelectric layer and an array of ultrasonic sensor pixels may be proximate a second side of the piezoelectric layer. In some instances, the first ultrasonic signals may be received by the ultrasonic sensor system electrode. In some examples, the method may involve performing an authentication process that is based, at least in part, on ultrasonic signals received via the array of ultrasonic sensor pixels. According to some examples, the method may involve causing the piezoelectric layer to transmit ultrasonic waves by applying a voltage to the ultrasonic sensor system electrode.

In some examples, the one or more first ultrasonic signal parameters and the one or more second ultrasonic signal parameters may include frequency, amplitude, phase and/or decay coefficient. According to some examples, acquiring the first ultrasonic signals and the second ultrasonic signals may involve controlling the ultrasonic sensor system to transmit ultrasonic waves according to each of a plurality of modes. Each of the modes may correspond with a different combination of ultrasonic sensor system parameters.

Some or all of the operations, functions and/or methods described herein may be performed by one or more devices according to instructions (e.g., software) stored on one or more non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. For example, the software may include instructions for controlling one or more devices to perform a method.

In some examples, the method may involve receiving ultrasonic sensor system temperature data from a temperature sensor configured to determine an ultrasonic sensor system temperature of an ultrasonic sensor system. The ultrasonic sensor system temperature data may, for example, indicate the ultrasonic sensor system temperature. In some examples, the method may involve acquiring first ultrasonic signals via the ultrasonic sensor system. In some instances, the first ultrasonic signals may correspond to reflections from a cover/air interface. The cover/air interface may be an interface between air and a cover of an apparatus that includes the ultrasonic sensor system.

In some examples, the method may involve determining one or more first ultrasonic signal parameters of the first ultrasonic signals. In some examples, the method may involve acquiring second ultrasonic signals from a target proximate the cover via the ultrasonic sensor system. The second ultrasonic signals may, in some instances, be received by an ultrasonic sensor system electrode and may correspond to reflections from a cover/target interface. In some examples, the method may involve determining one or more second ultrasonic signal parameters of the second ultrasonic signals. In some examples, the method may involve estimating, based at least in part on the one or more first ultrasonic signal parameters, the one or more second ultrasonic signal parameters, and the ultrasonic sensor system temperature, a target object temperature of the target object. According to some examples, the method may involve controlling a display to present a graphical user interface that indicates an estimated target object temperature.

According to some examples, the method may involve retrieving previously-acquired ultrasonic signal parameter data and previously-acquired temperature data from a memory and estimating the target object temperature based, at least in part, on the previously-acquired ultrasonic signal parameter data and the previously-acquired temperature data.

In some examples, the target object may be a body part of a user of the apparatus. In some examples, the previously-acquired ultrasonic signal parameter data and the previously-acquired temperature data may have been previously acquired from the user during a user calibration stage.

According to some examples, the ultrasonic sensor system may include a piezoelectric layer. The ultrasonic sensor system electrode may be proximate a first side of the piezoelectric layer and an array of ultrasonic sensor pixels may be proximate a second side of the piezoelectric layer. In some instances, the first ultrasonic signals may be received by the ultrasonic sensor system electrode. In some examples, the method may involve performing an authentication process that is based, at least in part, on ultrasonic signals received via the array of ultrasonic sensor pixels. According to some examples, the method may involve causing the piezoelectric layer to transmit ultrasonic waves by applying a voltage to the ultrasonic sensor system electrode.

In some examples, the one or more first ultrasonic signal parameters and the one or more second ultrasonic signal parameters may include frequency, amplitude, phase and/or decay coefficient. According to some examples, acquiring the first ultrasonic signals and the second ultrasonic signals may involve controlling the ultrasonic sensor system to transmit ultrasonic waves according to each of a plurality of modes. Each of the modes may correspond with a different combination of ultrasonic sensor system parameters.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

FIG. 4 shows an example of a data structure that may be used to determine one or more fingerprint sensor parameters based, at least in part, on the ultrasonic sensor system temperature data.

DETAILED DESCRIPTION

Figure 1:
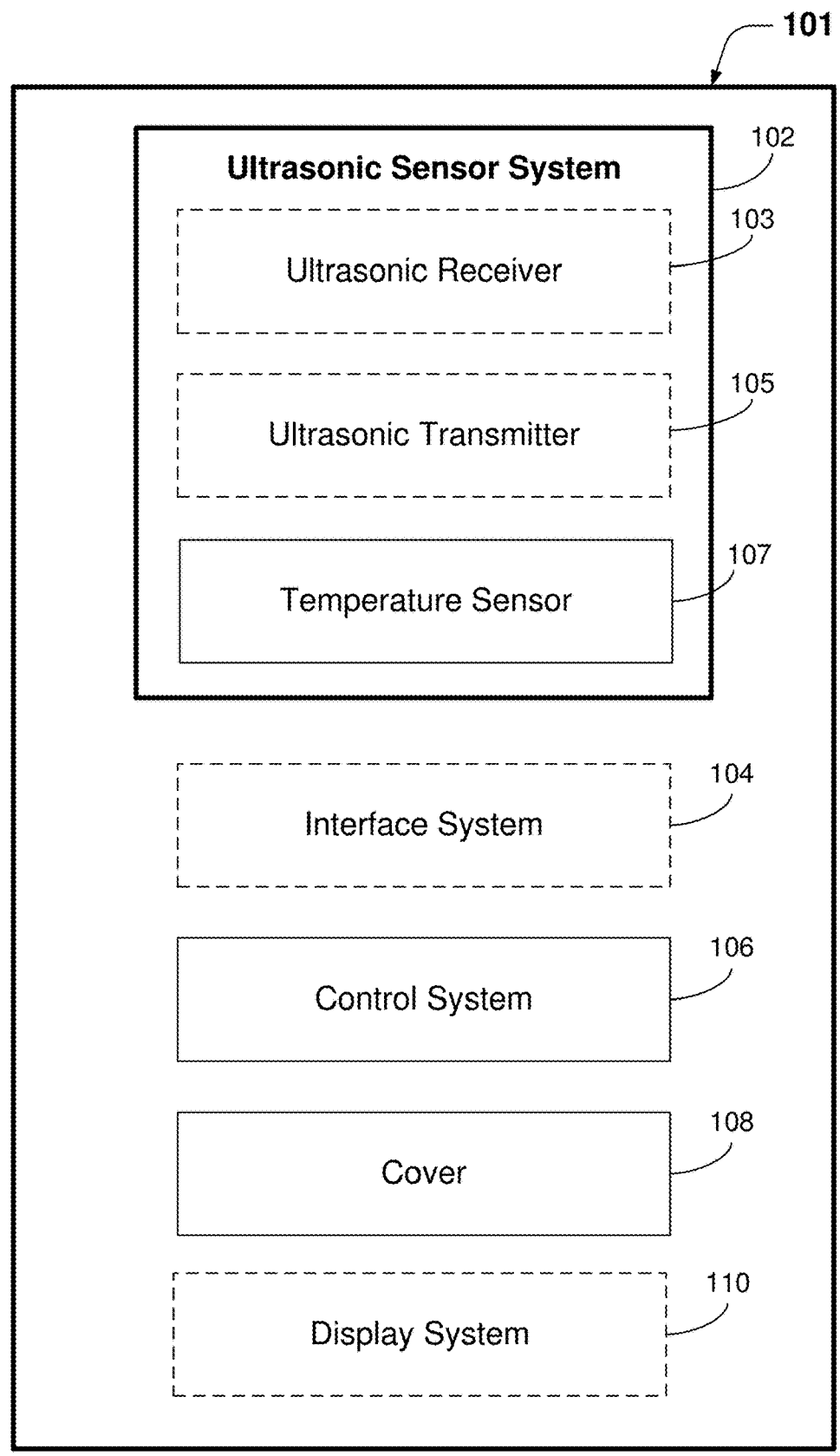
FIG. 1 is a block diagram that shows example components of an apparatus according to some disclosed implementations.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a biometric system as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

The Covid-19 pandemic has created increased interest in convenient ways to measure body temperature. In many instances, people may wish to measure their body temperature when they are away from home and do not have a thermometer available. Many people would prefer not to carry a thermometer or thermal camera with them. Some recently-deployed smart phones include a temperature sensor. However, adding a temperature sensor to a smart phone increases cost.

Some disclosed devices are capable of measuring, or estimating, a user's body temperature via an ultrasonic sensor system, such as an ultrasonic fingerprint sensor system. In some examples, an estimate of the user's body temperature may be based, at least in part, on a comparison of currently-obtained ultrasonic signal parameters, previously-acquired ultrasonic signal parameter data and previously-acquired temperature data corresponding to the previously-acquired ultrasonic signal parameter data.

Particular implementations of the subject matter described in this disclosure may be implemented to realize one or more of the following potential advantages. In some instances, a device (e.g., a smart phone) may require no new hardware for estimating a user's body temperature. Instead, some such implementations may include previously-deployed ultrasonic fingerprint sensor hardware configured to provide fingerprint authentication functionality. The ultrasonic fingerprint sensor system may, in some instances, be deployed in a smart phone. However, the control system of device (e.g., the smart phone) may be upgraded and configured to measure, or estimate, the user's body temperature via the ultrasonic fingerprint sensor system. Such implementations avoid the higher cost of including a temperature sensor in the device that is configured to measure the user's body temperature.

According to some examples, the ultrasonic sensor system may include a piezoelectric layer, an electrode proximate a first side of the piezoelectric layer and an array of ultrasonic sensor pixels proximate a second side of the piezoelectric layer. The ultrasonic signals that are used to estimate a person's temperature may, in some such examples, be received via the electrode. Such implementations are potentially advantageous for various reasons. One such potential advantage is that there may be a relatively higher signal-to-noise ratio if ultrasonic signals are received via the electrode instead of being received via the array of ultrasonic sensor pixels. Moreover, implementations in which ultrasonic signals can be received via the electrode instead of being received via the array of ultrasonic sensor pixels may be relatively faster, may use relatively less power and may be relatively less costly to operate.

FIG. 1 is a block diagram that shows example components of an apparatus according to some disclosed implementations. In this example, the apparatus 101 includes an ultrasonic sensor system 102, a control system 106 and a cover 108. In some implementations, the apparatus 101 may include an interface system 104 and/or a display system 110.

According to this example, the ultrasonic sensor system 102 is, or includes, an ultrasonic fingerprint sensor. In this example, the ultrasonic sensor system 102 includes a temperature sensor 107 that is configured to determine the temperature of the ultrasonic sensor system and to provide ultrasonic sensor system temperature data to the control system 106 indicating the ultrasonic sensor system temperature. Some alternative examples may not include a temperature sensor that is configured to determine the temperature of the ultrasonic sensor system. In some examples, as suggested by the dashed lines within the ultrasonic sensor system 102, the ultrasonic sensor system 102 may include an ultrasonic receiver 103 and a separate ultrasonic transmitter 105. In some such examples, the ultrasonic transmitter 105 may include an ultrasonic plane-wave generator.

However, various examples of ultrasonic fingerprint sensors are disclosed herein, some of which may include a separate ultrasonic transmitter 105 and some of which may not. Although shown as separate elements in FIG. 1, in some implementations the ultrasonic receiver 103 and the ultrasonic transmitter 105 may be combined in an ultrasonic transceiver system. For example, in some implementations, the ultrasonic sensor system 102 may include a piezoelectric receiver layer, such as a layer of polyvinylidene fluoride PVDF polymer or a layer of polyvinylidene fluoride-trifluoroethylene (PVDF-TrFE) copolymer. In some implementations, a separate piezoelectric layer may serve as the ultrasonic transmitter. In some implementations, a single piezoelectric layer may serve as both a transmitter and a receiver. In some implementations that include a piezoelectric layer, other piezoelectric materials may be used in the piezoelectric layer, such as aluminum nitride (AlN) or lead zirconate titanate (PZT). The ultrasonic sensor system 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, PMUT elements in a single-layer array of PMUTs or CMUT elements in a single-layer array of CMUTs may be used as ultrasonic transmitters as well as ultrasonic receivers.

Data received from the ultrasonic sensor system 102 may sometimes be referred to herein as "ultrasonic image data," "image data," etc., although the data will generally be received from the ultrasonic sensor system in the form of electrical signals. Accordingly, without additional processing such image data would not necessarily be perceivable by a human being as an image.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. According to some examples, the control system 106 may include a dedicated component for controlling the ultrasonic sensor system 102. The control system 106 also may include (and/or be configured for communication with) one or more memory devices, such as one or more random access memory (RAM) devices, read-only memory (ROM) devices, etc. Accordingly, the apparatus 101 may have a memory system that includes one or more memory devices, though the memory system is not shown in FIG. 1. The control system 106 may be configured for receiving and processing data from the ultrasonic sensor system 102. If the apparatus 101 includes a separate ultrasonic transmitter 105, the control system 106 may be configured for controlling the ultrasonic transmitter 105. In some implementations, functionality of the control system 106 may be partitioned between one or more controllers or processors, such as between a dedicated sensor controller and an applications processor of a mobile device.

Some implementations of the apparatus 101 may include an interface system 104. In some examples, the interface system 104 may include a wireless interface system. In some implementations, the interface system 104 may include a user interface system, one or more network interfaces, one or more interfaces between the control system 106 and a memory system, and/or one or more interfaces between the control system 106 and one or more external device interfaces (e.g., ports or applications processors).

The interface system 104 may be configured to provide communication (which may include wired or wireless communication, electrical communication, radio communication, etc.) between components of the apparatus 101. In some such examples, the interface system 104 may be configured to provide communication between the control system 106 and the ultrasonic sensor system 102. According to some such examples, the interface system 104 may couple at least a portion of the control system 106 to the ultrasonic sensor system 102, e.g., via electrically conducting material (e.g., via conductive metal wires or traces. If the apparatus 101 includes an ultrasonic transmitter 105 that is separate from the ultrasonic receiver 103, the interface system 104 may be configured to provide communication between at least a portion of the control system 106 and the ultrasonic transmitter 105. According to some examples, the interface system 104 may be configured to provide communication between the apparatus 101 and other devices and/or human beings. In some such examples, the interface system 104 may include one or more user interfaces. The interface system 104 may, in some examples, include one or more network interfaces and/or one or more external device interfaces (such as one or more universal serial bus (USB) interfaces or a serial peripheral interface (SPI)). In some implementations, the apparatus 101 may include a memory system. The interface system 104 may, in some examples, include at least one interface between the control system 106 and a memory system.

According to this example, the apparatus 101 includes a cover 108. The cover may or may not be made of a transparent material such as glass, depending on the particular implementation. The cover 108 may be formed of any appropriate material for the particular implementation, such as glass, a hard plastic, etc. If the cover 108 overlies a display, the cover 108 is preferably formed of transparent material. In some implementations, at least a portion of the cover 108 may not overly a display. According to some such examples, at least a portion of the ultrasonic sensor system 102 may reside on a side or the back of an apparatus that includes ultrasonic sensor system 102, such as a side or the back of a mobile device such as a smart phone. In some such implementations, at least a portion of the cover 108 may be optically opaque. In some such examples, at least a portion of the cover 108 may be formed of metal, opaque plastic, a ceramic material, etc.

In some implementations, the apparatus 101 may include a display system 110. For example, the apparatus 101 may include layers of a display, which layers may be referred to herein as a "display stack." In some examples, the display system 110 may be, or may include, a light-emitting diode (LED) display, such as an organic light-emitting diode (OLED) display.

The apparatus 101 may be used in a variety of different contexts, some examples of which are disclosed herein. For example, in some implementations a mobile device may include at least a portion of the apparatus 101. In some implementations, a wearable device may include at least a portion of the apparatus 101. The wearable device may, for example, be a bracelet, an armband, a wristband, a ring, a headband or a patch. In some implementations, the control system 106 may reside in more than one device. For example, a portion of the control system 106 may reside in a wearable device and another portion of the control system 106 may reside in another device, such as a mobile device (e.g., a smartphone). The interface system 104 also may, in some such examples, reside in more than one device.

Figure 2:
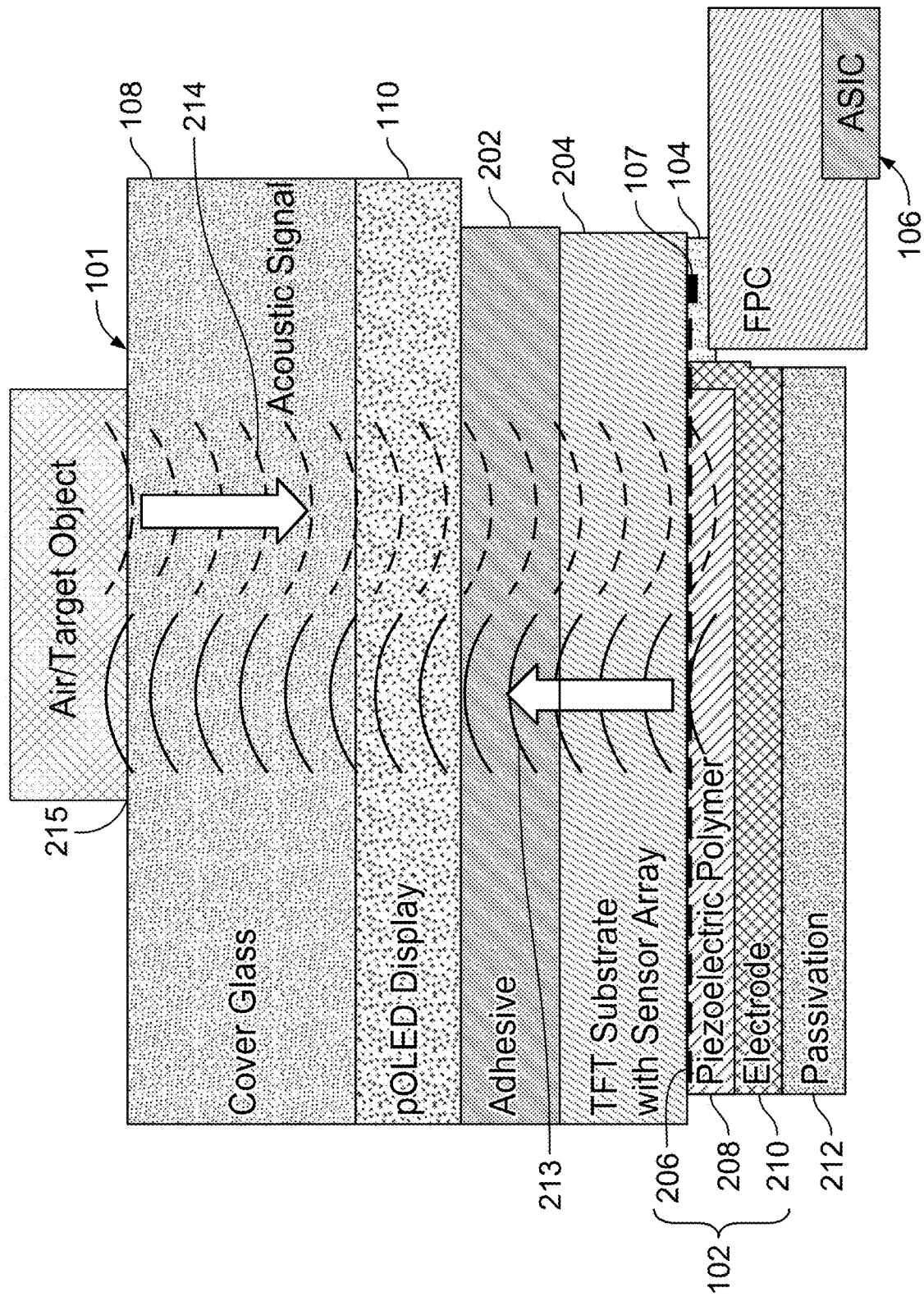
FIG. 2 shows example components of an apparatus according to some disclosed implementations.

FIG. 2 shows example components of an apparatus according to some disclosed implementations. As with other disclosed implementations, the types, number and arrangement of elements, as well as the dimensions of elements, are merely examples. According to this example, the apparatus 101 is configured to perform at least some of the methods disclosed herein. According to this implementation, the apparatus 101 has an ultrasonic sensor system 102 that includes a piezoelectric layer 208, an electrode layer 210 on one side of the piezoelectric layer 208 and an array of sensor pixels 206 on a second and opposing side of the piezoelectric layer 208. In this implementation, the piezoelectric layer 208 is an ultrasonic transceiver layer that includes one or more piezoelectric polymers. According to this example, the ultrasonic sensor system 102 includes a temperature sensor 107 that is configured to determine the temperature of the ultrasonic sensor system 102 and to provide ultrasonic sensor system temperature data to the control system 106 indicating the ultrasonic sensor system temperature. In some implementations, the temperature sensor 107 may be, or may include, a temperature sensing diode. In this example, the temperature sensor 107 is electrically connected to the thin-film transistor (TFT) layer 204, e.g., via a conductive element such as a pin.

According to this example, the electrode layer 210 resides between a passivation layer 212 and the piezoelectric layer 208. In some examples, passivation layer 212 may include an adhesive, such as an epoxy film, a polymer layer (such as a polyethylene terephthalate (PET) layer), etc.

In this example the TFT layer 204 includes a TFT substrate and circuitry for the array of sensor pixels 206. The TFT layer 204 may be a type of metal-oxide-semiconductor field-effect transistor (MOSFET) made by depositing thin films of an active semiconductor layer as well as a dielectric layer and metallic contacts over a TFT substrate. In some examples, the TFT substrate may be a non-conductive material such as glass.

In this example, the apparatus 101 includes a display system 110, which includes an OLED display in this instance. Here, the OLED display is attached to the TFT layer 204 via an adhesive layer 202.

According to this implementation, the TFT layer 204, the array of sensor pixels 206 and the electrode are electrically coupled to at least a portion of the control system 106 and one side of the ultrasonic transceiver layer 101 via a portion of the interface system 104, which includes electrically conducting material and a flexible printed circuit (FPC) in this instance.

In this example, the apparatus 101 is configured to perform at least some of the methods disclosed herein. In this example, the control system 106 is configured to control the ultrasonic sensor system 102 to transmit one or more ultrasonic waves 213. According to this example, the ultrasonic wave(s) 213 are transmitted through the TFT layer 204, the OLED display and the cover 108. According to this example, reflections 214 of the ultrasonic wave(s) 213 are caused by acoustic impedance contrast at (or near) the interface 215 between the outer surface of the cover 108 and whatever is in contact with the outer surface, which may be air or the surface of a target object, such as the ridges and valleys of a fingerprint, etc. (As used herein, the term "finger" may refer to any digit, including a thumb. Accordingly, a thumbprint will be considered a type of "fingerprint.")

According to some examples, reflections 214 of the ultrasonic wave(s) 213 may be used to estimate the body temperature of a person whose finger is on an outer surface of the apparatus 101, e.g., on the cover 108. In some such examples, the reflections 214 may be detected by the electrode layer 210. Corresponding ultrasonic signals may be provided to the control system 106. In some such implementations, reflections 214 corresponding to a cover/air interface may be detected by the electrode layer 210 and corresponding background ultrasonic signals may be provided to the control system 106. In some such implementations, ultrasonic signals that are used by the control system 106 for fingerprint-based authentication may be based on reflections 214 from a cover/finger interface that are detected by the array of sensor pixels 206.

Figure 3:
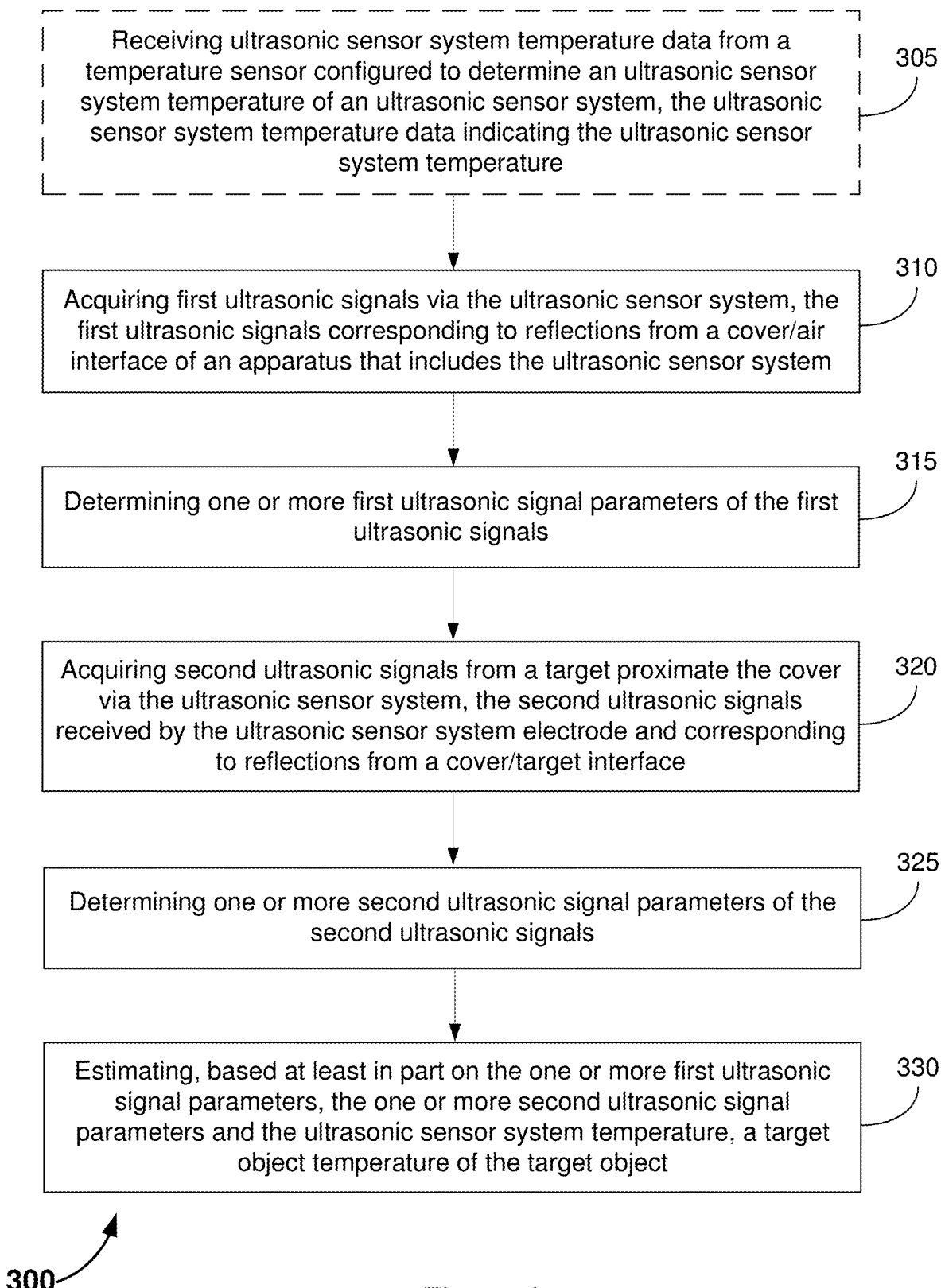
FIG. 3 is a flow diagram that provides examples of operations according to some disclosed methods.

FIG. 3 is a flow diagram that provides examples of operations according to some disclosed methods. The blocks of FIG. 3 may, for example, be performed by the apparatus 101 of FIG. 1 or 2, or by a similar apparatus. As with other methods disclosed herein, the method outlined in FIG. 3 may include more or fewer blocks than indicated. For example, some implementations may omit block 305. Moreover, the blocks of methods disclosed herein are not necessarily performed in the order indicated. In some instances, one or more blocks may be performed concurrently.

In this example, block 305 involves receiving ultrasonic sensor system temperature data from a temperature sensor configured to determine an ultrasonic sensor system temperature of an ultrasonic sensor system. In this example, the ultrasonic sensor system temperature data indicates the ultrasonic sensor system temperature, e.g., the temperature of the ultrasonic sensor system 102 of FIG. 1 or FIG. 2. For example, block 305 may involve the control system 106 of FIG. 1 or FIG. 2 receiving ultrasonic sensor system temperature data from the temperature sensor 107.

In some examples, method 300 involves determining at least one new ultrasonic fingerprint sensor parameter based, at least in part, on the ultrasonic sensor system temperature data. In some such examples, method 300 may involve determining at least one new ultrasonic fingerprint sensor parameter if the ultrasonic sensor system temperature data indicates that the ultrasonic sensor system temperature has changed by more than a threshold amount (e.g., 3 degrees Celsius, 4 degrees Celsius, 5 degrees Celsius, etc.). The at least one new ultrasonic fingerprint sensor parameter may, for example, include a range gate delay, a frequency of a transmitted ultrasonic wave or a bias voltage. Determining the at least one new ultrasonic fingerprint sensor parameter may, in some instances, involve obtaining the at least one new ultrasonic fingerprint sensor parameter from a portion of a data structure corresponding to the temperature. The data structure may be, or may include, a look-up table. For example, method 300 may involve a control system querying a data structure that includes temperature data and one or more corresponding ultrasonic fingerprint sensor parameters.

FIG. 4 shows an example of a data structure that may be used to determine one or more fingerprint sensor parameters based, at least in part, on the ultrasonic sensor system temperature data. In this example, the data structure 405 includes fingerprint sensor parameters and corresponding temperatures in degrees Celsius. According to this example, the fingerprint sensor parameters include frequency, range gate delay (RGD) and bias voltage. RGD may, for example, correspond to a time interval between the transmission of an ultrasonic wave (or the time at which a voltage is applied to cause the transmission of an ultrasonic wave) and the beginning of a time window during which reflected ultrasonic waves are sampled, which may be referred to as a range gate window or RGW. In this example, the data structure 405 is a look-up table (LUT).

In some examples, method 300 may involve querying a data structure such as the data structure 405 and determining one or more ultrasonic fingerprint sensor parameters corresponding to a temperature that is determined in block 305. In some examples, the data structure may include transient temperature values and one or more types of corresponding ultrasonic fingerprint sensor parameters. Some implementations involve determining ultrasonic fingerprint sensor parameters for corresponding transient temperature values.

Returning to FIG. 3, according to this implementation block 310 involves acquiring first ultrasonic signals via the ultrasonic sensor system. In some examples, the control system 106 of FIG. 1 or FIG. 2 may control the ultrasonic sensor system 102 to acquire the first ultrasonic signals in block 310. In this example, the first ultrasonic signals corresponding to reflections from a cover/air interface of an apparatus that includes the ultrasonic sensor system. As used herein, the word "first" does not necessarily have a temporal meaning. For example, the phrase "first ultrasonic signals" is not necessarily intended to mean (and in general will not mean) the first ultrasonic signals ever to be acquired via the ultrasonic sensor system. Instead, terms such as "first," "second," etc., as used herein are primarily (and in some instances, solely) intended to identify specific features, or types of features, and/or to differentiate features from one another.

In some examples, acquiring the first ultrasonic signals may involve controlling the ultrasonic sensor system to transmit ultrasonic waves according to each of a plurality of modes. In some implementations, each of the modes may correspond with a different combination of ultrasonic sensor system parameters. Some examples of modes are described below.

According to some implementations, the first ultrasonic signals corresponding to reflections from a cover/air interface are for determining sets of "background" (BG) ultrasonic image data (e.g., for a plurality of modes) that correspond to BG noise. The ultrasonic image data corresponding to BG noise may be stored in a memory and subsequently subtracted from ultrasonic image data obtained with a target object on the surface, in order to increase the signal-to-noise ratio of the resulting ultrasonic image data.

Figure 10A:
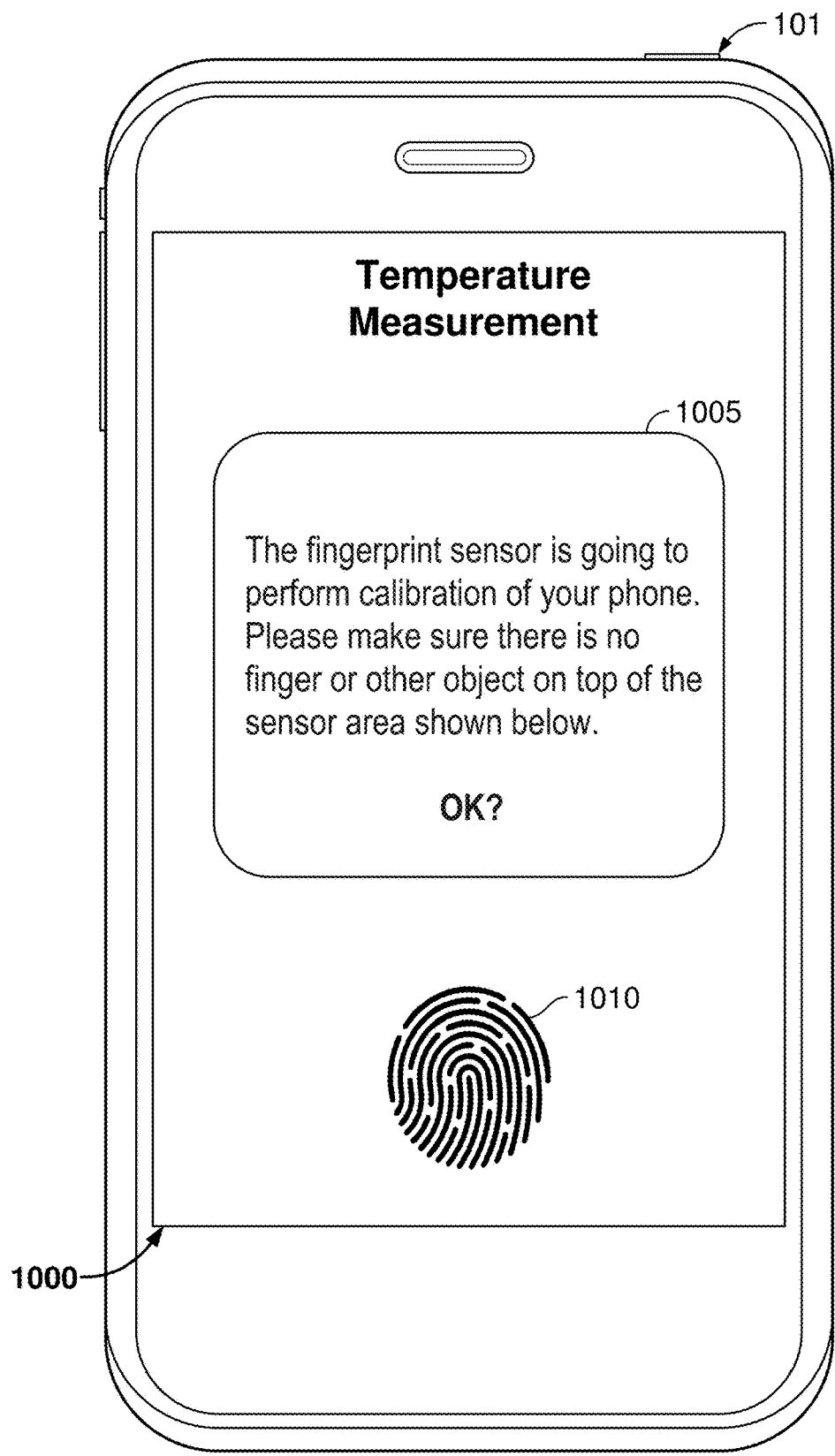
FIGS. 10A, 10B, 10C and 10D show examples of graphical user interfaces (GUIs) that may be presented during a process of implementing the method 300 according to some examples.

Some examples may involve controlling (e.g., by a control system such as the control system 106) a user interface system (e.g., a user interface system portion of the interface system 104 of FIG. 1) to provide one or more user prompts. Some examples are shown in FIG. 10A et seq. and are described below. According to some implementations, the user interface system may include a display stack, which may be a component of the display system 110 of FIG. 1. In some implementations, the cover of an apparatus that includes the ultrasonic sensor system may be a cover glass. In some such implementations, at least a portion of the display stack may reside between the cover glass and the ultrasonic sensor system.

In this example, block 315 involves determining one or more first ultrasonic signal parameters of the first ultrasonic signals. In some instances, control system 106 of FIG. 1 or FIG. 2 may determine the first ultrasonic signal parameters in block 315. According to some examples, the first ultrasonic signal parameters may include the frequency content, amplitude and/or phase of the first ultrasonic signals. In some implementations the first ultrasonic signal parameters may include a decay coefficient corresponding to the first ultrasonic signals.

According to this implementation, block 320 involves acquiring second ultrasonic signals from a target proximate the cover via the ultrasonic sensor system. The target may, in some instances, be a finger on the cover. According to this example, the second ultrasonic signals correspond to reflections from a cover/target interface. Alternatively, or additionally, in some examples, the second ultrasonic signals correspond to reflections from within a target object, such as a finger, that is on the cover.

In some examples, the second ultrasonic signals may be received (or may have been received) by an ultrasonic sensor system electrode. For example, the second ultrasonic signals may be, or may have been, acquired via the electrode 210 of FIG. 2, or via a similar electrode. According to some such examples, a control system may be configured to cause a piezoelectric layer (such as the piezoelectric layer 208 of FIG. 2) to transmit ultrasonic waves by applying a voltage to the same ultrasonic sensor system electrode that is used to receive ultrasonic signals corresponding to reflections caused by these transmitted ultrasonic waves. Ultrasonic signals that are received by an ultrasonic sensor system electrode such as the electrode 210 of FIG. 2 may be referred to herein as A-line signals, one example of which is described below with reference to FIG. 5.

Implementations in which ultrasonic signals are obtained via an ultrasonic sensor system electrode such as the electrode 210 of FIG. 2 are potentially advantageous, at least in part because there may be a relatively higher signal-to-noise ratio if ultrasonic signals are received via the electrode instead of being received via the array of ultrasonic sensor pixels and the corresponding TFT circuitry. Moreover, implementations in which ultrasonic signals can be received via the electrode instead of being received via the array of ultrasonic sensor pixels may be relatively faster, may use relatively less power and may be relatively less costly to operate. In some implementations, the first ultrasonic signals also may have been acquired via the electrode 210 of FIG. 2, or via a similar electrode. However, in alternative implementations, the first ultrasonic signals and/or the second ultrasonic signals may be received via one or more of the ultrasonic sensor pixels.

In some examples, acquiring the second ultrasonic signals may involve controlling the ultrasonic sensor system to transmit ultrasonic waves according to each of a plurality of modes. In some implementations, each of the modes may correspond with a different combination of ultrasonic sensor system parameters. Some examples of modes are described below.

In some examples, method 300 may involve controlling the display stack to present a graphical user interface that indicates an ultrasonic sensor system area. According to some examples, method 300 may involve controlling the display stack to present text prompting the user to ensure that there is no object on or proximate the ultrasonic sensor system area prior to acquiring ultrasonic signals corresponding to reflections from a cover/air interface, e.g., prior to acquiring the first ultrasonic signals and/or during what may be referred to herein as a "user calibration stage." Some examples are described below with reference to FIGS. 10A and 11A. In some examples, method 300 may involve controlling the display stack to present text prompting the user to position a body part on the ultrasonic sensor system area prior to acquiring the second ultrasonic signals and/or during a user calibration stage. Some examples are described below with reference to FIGS. 10C and 11C.

In this example, block 325 involves determining one or more second ultrasonic signal parameters of the second ultrasonic signals. In some instances, control system 106 of FIG. 1 or FIG. 2 may determine the second ultrasonic signal parameters in block 325. According to some examples, the second ultrasonic signal parameters may include the frequency content, amplitude and/or phase of the second ultrasonic signals. In some implementations the second ultrasonic signal parameters may include a decay coefficient corresponding to the second ultrasonic signals.

According to this example, block 330 involves estimating (e.g., by a control system such as the control system 106 of FIG. 1), based at least in part on the one or more first ultrasonic signal parameters, the one or more second ultrasonic signal parameters and the ultrasonic sensor system temperature, a target object temperature of the target object. In some examples, block 330 may involve estimating (e.g., by a control system such as the control system 106 of FIG. 1) the body temperature of a person whose finger or other body part (e.g., the person's forehead, palm, wrist, etc.) is the target object.

In some implementations, block 330 may involve retrieving (e.g., by a control system such as the control system 106) previously-acquired ultrasonic signal parameter data and previously-acquired temperature data from a memory. According to some examples, block 330 may involve estimating the target object temperature based, at least in part, on the previously-acquired ultrasonic signal parameter data and the previously-acquired temperature data.

The previously-acquired ultrasonic signal parameter data may correspond with the previously-acquired temperature data. Some examples are described below. The previously-acquired ultrasonic signal parameter data may, in some implementations, have been acquired during what may be referred to herein as an "initial stage." According to some such implementations, the previously-acquired ultrasonic signal parameter data and the previously-acquired temperature data obtained during the initial stage were not previously acquired from the current owner and/or user of a device that is implementing the method 300.

Instead, during some implementations of the initial stage, the previously-acquired ultrasonic signal parameter data and the previously-acquired temperature data were acquired from other people. In some implementations, the previously-acquired ultrasonic signal parameter data and the previously-acquired temperature data may have been obtained from tens, hundreds or thousands of other people. In some such implementations, the previously-acquired ultrasonic signal parameter data and the previously-acquired temperature data may have been obtained prior to the deployment of a device configured to estimate, based at least in part on ultrasonic signal parameters, a target object temperature of the target object. In some such implementations, at least some of the previously-acquired ultrasonic signal parameter data and the previously-acquired temperature data may have been stored in a memory of a device configured to estimate, based at least in part on ultrasonic signal parameters, a target object temperature of the target object. In some examples, the previously-acquired ultrasonic signal parameter data and the previously-acquired temperature data may have been acquired via a plurality of devices.

According to some examples, the previously-acquired ultrasonic signal parameter data may have been determined based on ultrasonic signals received by an ultrasonic sensor system configured to transmit ultrasonic waves according to each of a plurality of modes. Each of the modes may correspond with a different combination of ultrasonic sensor system parameters. Sets of ultrasonic sensor system parameters corresponding to four modes are shown below in Table 1.

TABLE 1

| Mode | Freq (kHz) | Diff. Voltage (V) | Amplitude gain (dB) |
|---|---|---|---|
| 1 | 8.5 | 3 | 2 |
| 2 | 9 | 0 | 4 |
| 3 | 10 | 0 | 1 |
| 4 | 13 | 3 | 0 |

In this example, each of modes 1-4 corresponds to a set of ultrasonic sensor system parameters that includes a frequency, a differential voltage and an amplitude gain. According to this example, the ultrasonic sensor system parameters shown in Table 1 are for controlling an ultrasonic sensor system for the transmission of ultrasonic waves. The differential voltages and amplitudes shown in Table 1 are in addition to baseline or default levels used for transmitting ultrasonic waves. Other examples may involve more or fewer modes and/or modes having different ultrasonic sensor system parameters.

According to some implementations, the previously-acquired ultrasonic signal parameter data may correspond to A-line signals received via an ultrasonic sensor electrode, such as the electrode 210 shown in FIG. 2.

Figure 5:
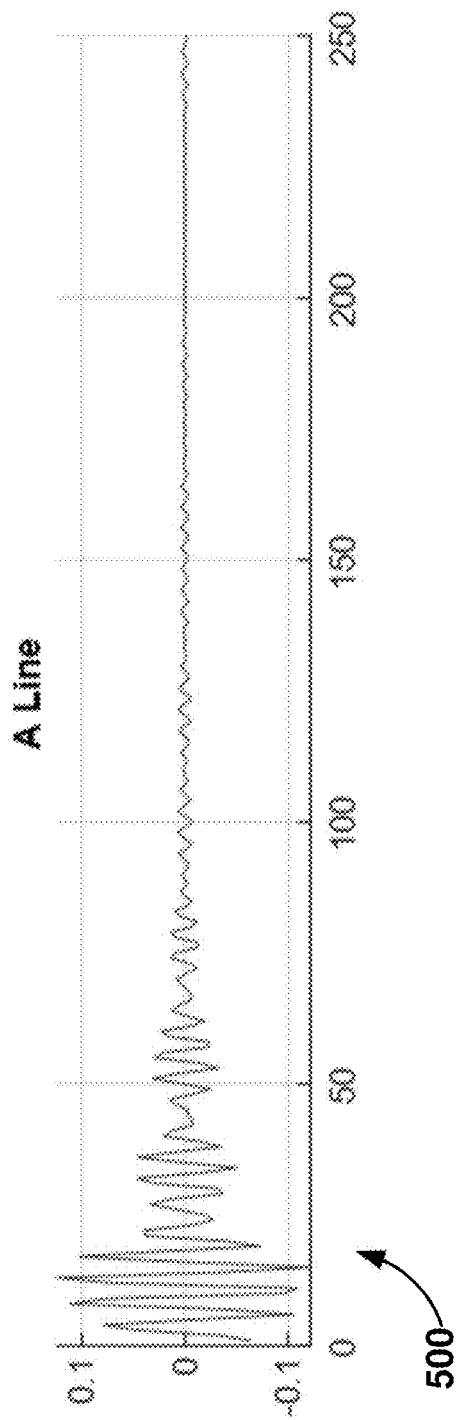
FIG. 5 is a graphical representation of an A-line signal according to one example.

FIG. 5 is a graphical representation of an A-line signal according to one example. The vertical axis of the graph 500 indicates amplitude, in decibels, and the horizontal axis indicates time, in microseconds.

According to some implementations, an A-line signal may be represented according to a sum of exponentially decaying sinusoids. In one such example, an A-line signal may be represented as follows:

$$\sum_{k=1}^{N} A_k e^{\beta_k t} \sin(B f_k t + \varphi_k) \quad \text{Equation 1}$$

In Equation 1, $f_k$ represents frequency, $A_k$ represents amplitude, $\varphi_k$ represents phase, $\beta_k$ represents a decay coefficient, t represents time and B represents a constant. In some examples, B may be a value between 1 and 10, e.g., 4, 5, 6 or 7. The subscript k refers to a particular sinusoid, each of which may in some instances correspond to a particular mode.

FIGS. 6, 7, 8 and 9 are graphs that show examples of how elements of Equation 1 change according to mode and temperature. In FIGS. 6-9, the curves 340 correspond to a first transmission mode (e.g., mode 1 of Table 1), the curves 345 correspond to a second transmission mode (e.g., mode 2 of Table 1), the curves 350 correspond to a third transmission mode (e.g., mode 3 of Table 1) and the curves 355 correspond to a fourth transmission mode (e.g., mode 4 of Table 1).

Figure 6:
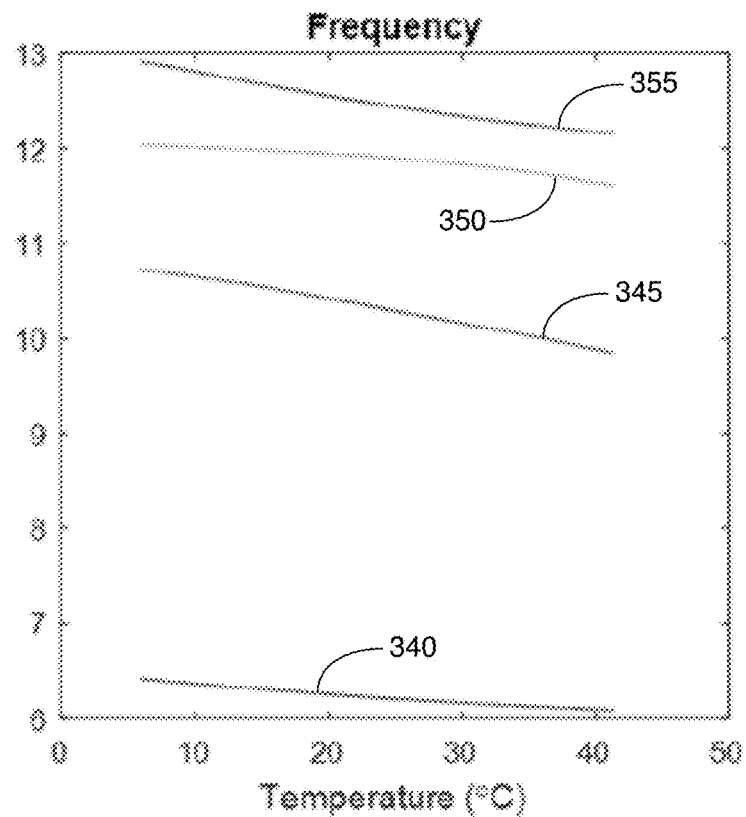
FIG. 6 shows examples of how the frequencies of received A-line signals change according to mode and according to the body temperature of a person from whose body part (e.g., finger, forehead, wrist, etc.) the data were obtained.

FIG. 6 shows examples of how the frequencies of received A-line signals change according to mode and according to the body temperature of a person from whose body part (e.g., finger, forehead, wrist, etc.) the data were obtained. According to some implementations, the ultrasonic signal parameter data and temperature data obtained during the initial stage may include temperature/frequency pairs corresponding to the curves of FIG. 6 and/or temperature/frequency pairs corresponding to other modes. These temperature/frequency pairs may be stored in a memory.

Figure 7:
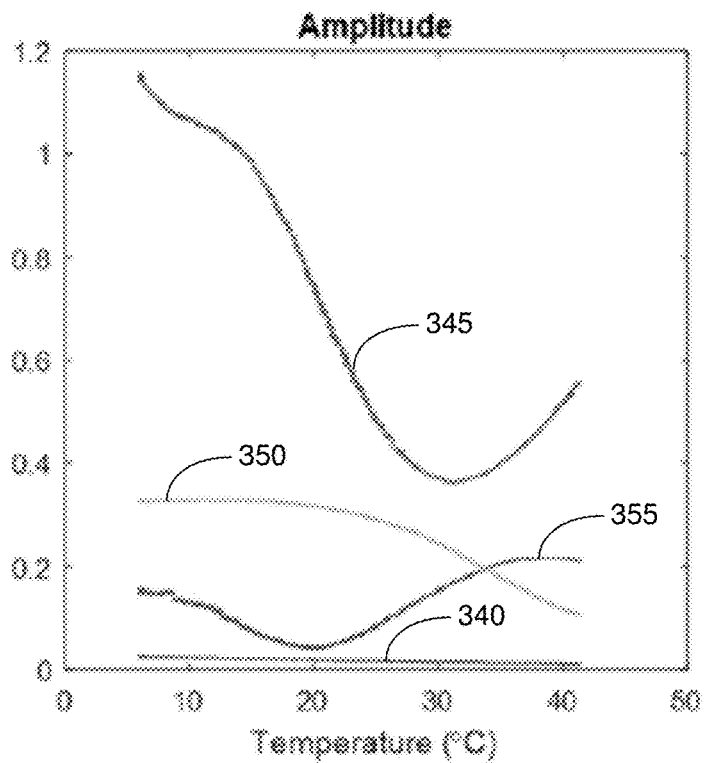
FIG. 7 shows examples of how the amplitudes of the received A-line signals change according to mode and body temperature.

FIG. 7 shows examples of how the amplitudes of the received A-line signals change according to mode and body temperature. In some implementations, the ultrasonic signal parameter data and temperature data obtained during the initial stage may include temperature/amplitude pairs corresponding to the curves of FIG. 7 and/or temperature/amplitude pairs corresponding to other modes. These temperature/amplitude pairs may be stored in a memory.

Figure 8:
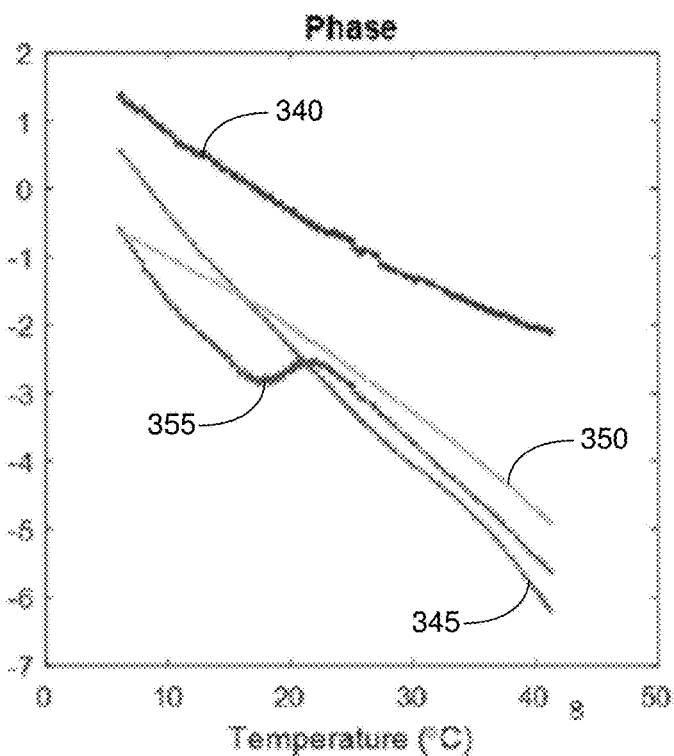
FIG. 8 shows examples of how the phases of the received A-line signals change according to mode and body temperature.

FIG. 8 shows examples of how the phases of the received A-line signals change according to mode and body temperature. In some examples, the ultrasonic signal parameter data and temperature data obtained during the initial stage may include temperature/phase pairs corresponding to the curves of FIG. 7 and/or temperature/phase pairs corresponding to other modes. These temperature/phase pairs may be stored in a memory.

Figure 9:
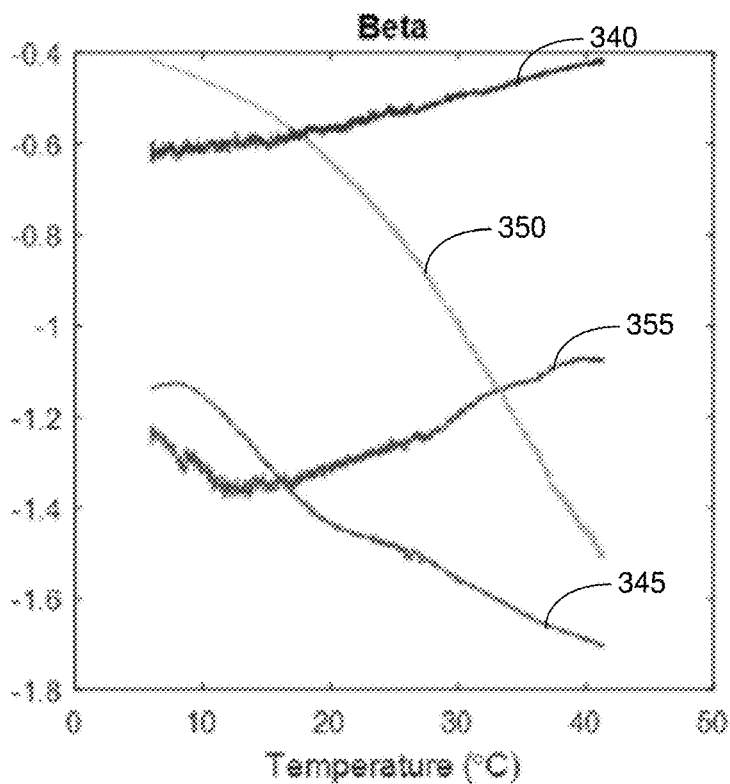
FIG. 9 shows examples of how the decay coefficients corresponding to the received A-line signals change according to mode and body temperature.

FIG. 9 shows examples of how the decay coefficients corresponding to the received A-line signals change according to mode and body temperature. According to some implementations, the ultrasonic signal parameter data and temperature data obtained during the initial stage may include temperature/decay coefficient pairs corresponding to the curves of FIG. 6 and/or temperature/decay coefficient pairs corresponding to other modes. These temperature/decay coefficient pairs may be stored in a memory.

FIGS. 10A, 10B, 10C and 10D show examples of graphical user interfaces (GUIs) that may be presented during a process of implementing the method 300 according to some examples. In the example shown in FIG. 10A, the GUI 1000 includes a message area 1005 and indicates an ultrasonic sensor system area 1010. In this example, the message area 1005 is presenting information and a prompt relating to acquiring the above-described "first ultrasonic signals" via an ultrasonic sensor system. Because the first ultrasonic signals are intended to include reference or "background" ultrasonic signals corresponding to reflections from a cover/air interface, the message area 1005 includes a prompt to ensure that there is no finger or other object on the ultrasonic sensor system area 1010 prior to implementing block 310 of FIG. 3, prior to implementing block 305, or as part of the process of implementing block 305 and/or 310.

In some implementations, the message area 1005 may be a virtual button with which a user may interact, e.g., by touching the message area 1005, in order to indicate that there is no finger or other object on the ultrasonic sensor system area 1010. In some such implementations, the apparatus 101 may include a touch screen, e.g., a touch screen overlying the display that is presenting the GUI 1000. A control system may be configured to interpret a touch in the message area 1005 as a response to at least a portion of the text in the message area 1005, e.g., as an affirmation that there is no finger or other object on the ultrasonic sensor system area 1010.

Figure 10B:
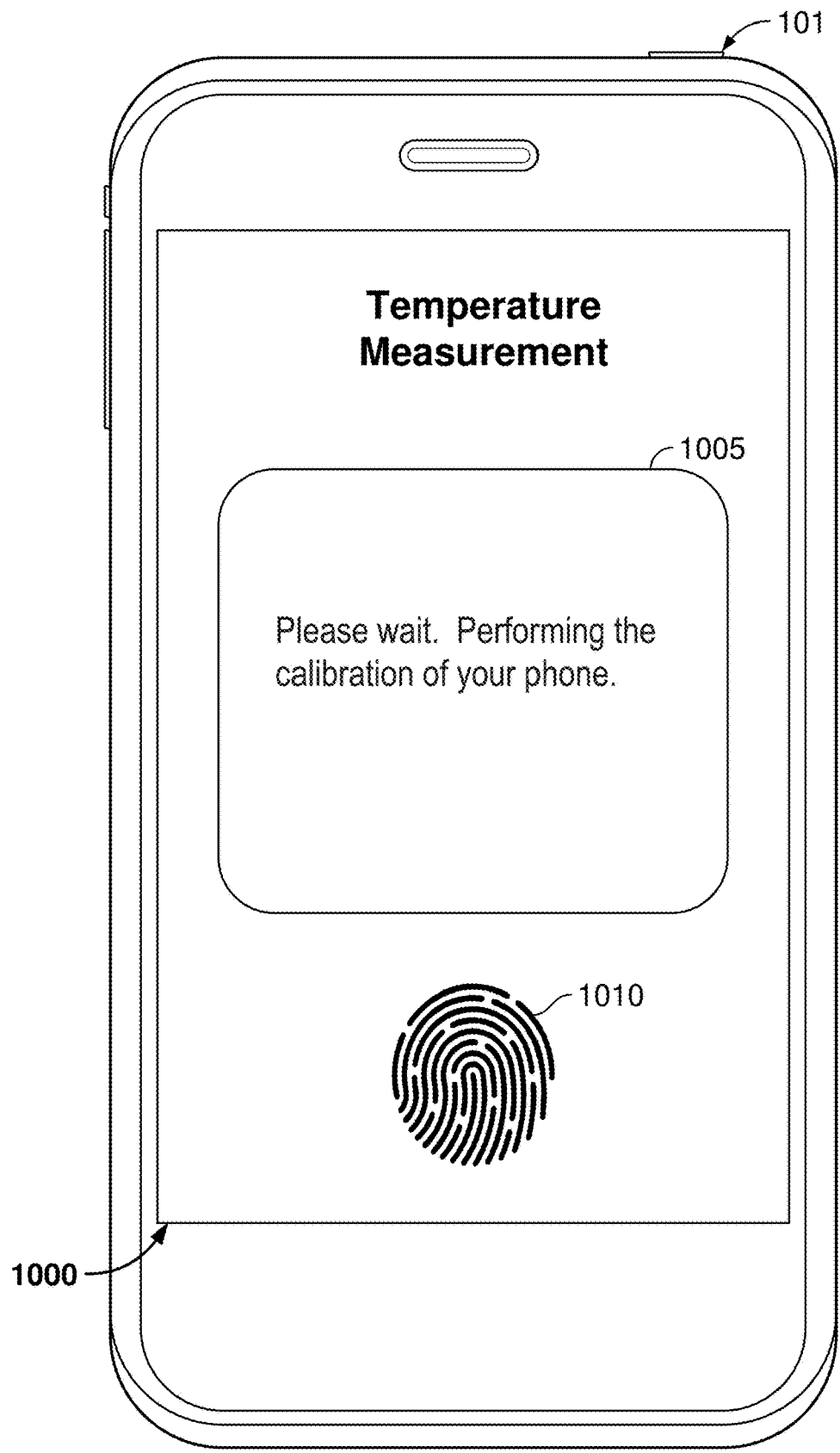

FIG. 10B shows an example of text that may be presented in the message area 1005 while the apparatus 101 is calibrating an ultrasonic sensor system. The text shown in the message area 1005 may, for example, be presented at a time during which background ultrasonic signals corresponding to reflections from a cover/air interface are obtained in block 310 of FIG. 3 and/or during which first ultrasonic signal parameters are being determined in block 315. In some examples, the text shown in the message area 1005 may be presented at a time during which ultrasonic sensor system temperature data are being obtained in block 305.

Figure 10C:
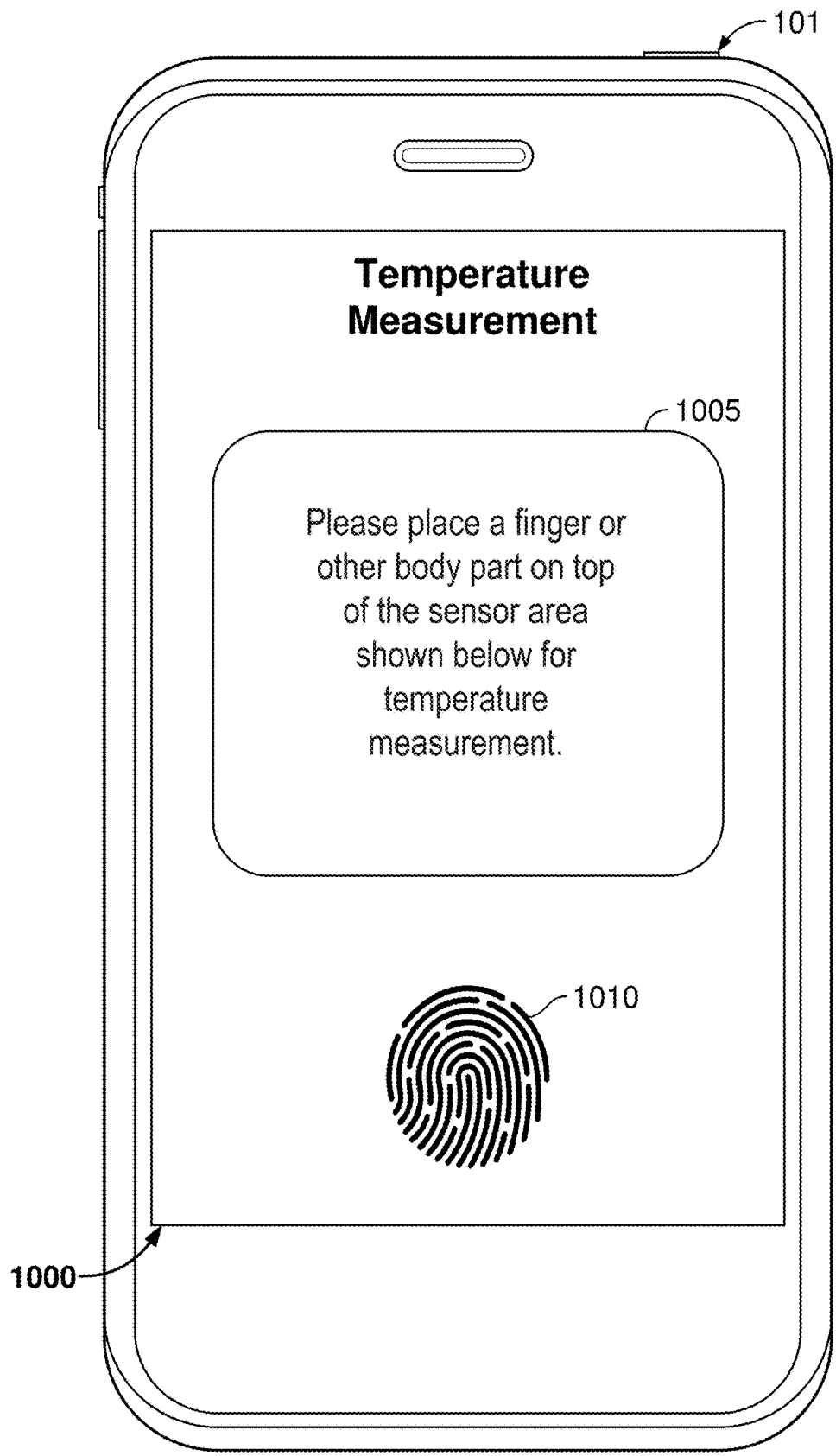
Figure 11A:
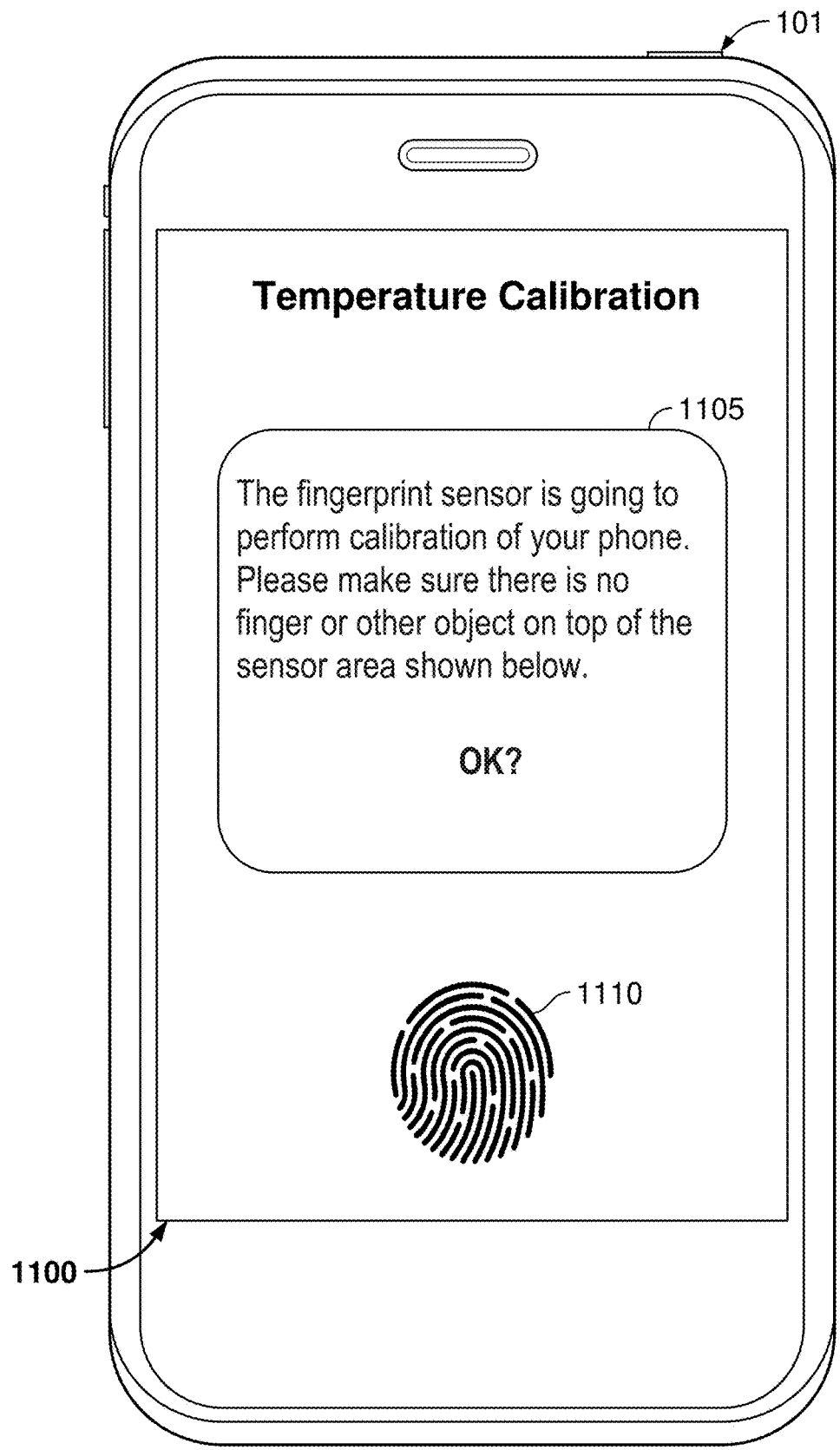
FIGS. 11A, 11B, 11C and 11D show examples of GUIs that may be presented during a user calibration process according to some examples.

FIG. 10C shows an example of a textual prompt that may be presented in the message area 1005 prior to obtaining second ultrasonic signals corresponding to a cover/target interface. In this example, a user is prompted to place a finger or other body part on the ultrasonic sensor system area 1010. In some alternative implementations, the text presented in the message area 1005 may provide other examples of suitable body parts, such as a user's forehead, wrist, ear, etc. According to some implementations, the ultrasonic sensor system area 1010 may be larger than that indicated in FIG. 10C. In some such implementations, the ultrasonic sensor system area 1010 may be coextensive with half or more of the display area of the apparatus 101. After the user places the body part on the ultrasonic sensor system area 1010, in some examples the second ultrasonic signals may be acquired, e.g., as described above with reference to block 320 of FIG. 3. According to some such examples, the second ultrasonic signals may be received by the ultrasonic sensor system electrode.

Figure 10D:
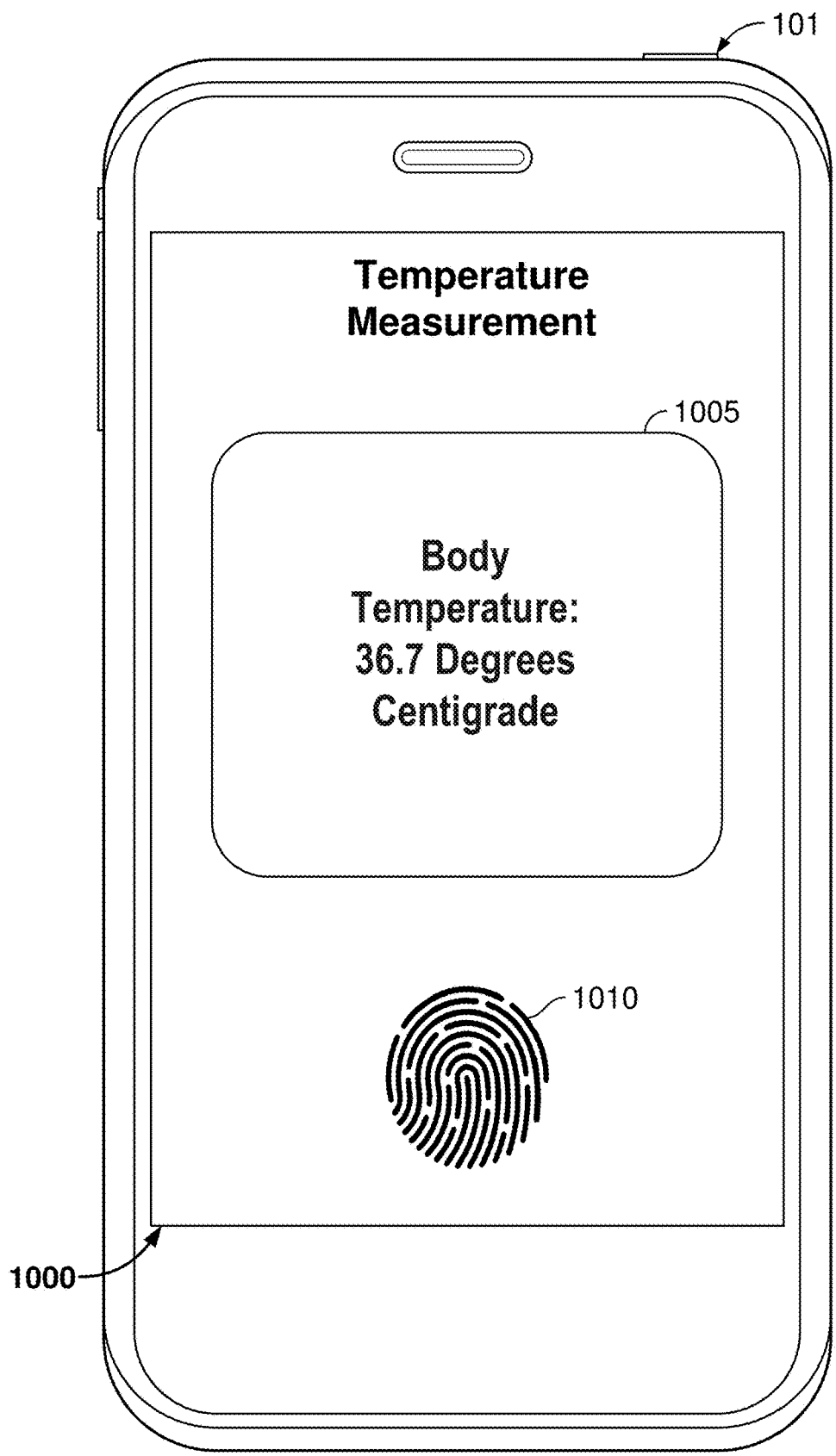

FIG. 10D shows an example of text that may be presented in the message area 1005 after blocks 325 and 330 of method 300 have been performed. In this example, the user's estimated body temperature is presented in the message area 1005.

According to some such implementations, at least some of the previously-acquired ultrasonic signal parameter data and/or the previously-acquired temperature data may have been previously acquired from the user (e.g., via the control system) during what may be referred to herein as a "user calibration stage." During a user calibration stage, in some implementations the user will be prompted to measure and input the user's current body temperature. In some user calibration stage examples, background ultrasonic signals and user body part ultrasonic signals will also be acquired. According to some examples, method 300 may involve controlling the display stack to present text prompting the user to ensure that there is no object on or proximate the ultrasonic sensor system area prior to acquiring ultrasonic signals corresponding to reflections from a cover/air interface during a user calibration stage.

FIGS. 11A, 11B, 11C and 11D show examples of graphical user interfaces (GUIs) that may be presented during a user calibration process according to some examples. In the example shown in FIG. 11A, the GUI 1100 includes a message area 1105 and indicates an ultrasonic sensor system area 1110. In this example, the message area 1105 is presenting information and a prompt relating to acquiring reference or "background" ultrasonic signals corresponding to reflections from a cover/air interface during a user calibration process. Here, the message area 1105 includes a prompt to ensure that there is no finger or other object on the ultrasonic sensor system area 1110.

In some implementations, the message area 1105 may be a virtual button with which a user may interact, e.g., by touching the message area 1105, in order to indicate that there is no finger or other object on the ultrasonic sensor system area 1110. In some such implementations, the apparatus 101 may include a touch screen, e.g., a touch screen overlying the display that is presenting the GUI 1100. A control system may be configured to interpret a touch in the message area 1105 as a response to at least a portion of the text in the message area 1105, e.g., as an affirmation that there is no finger or other object on the ultrasonic sensor system area 1110.

Figure 11B:
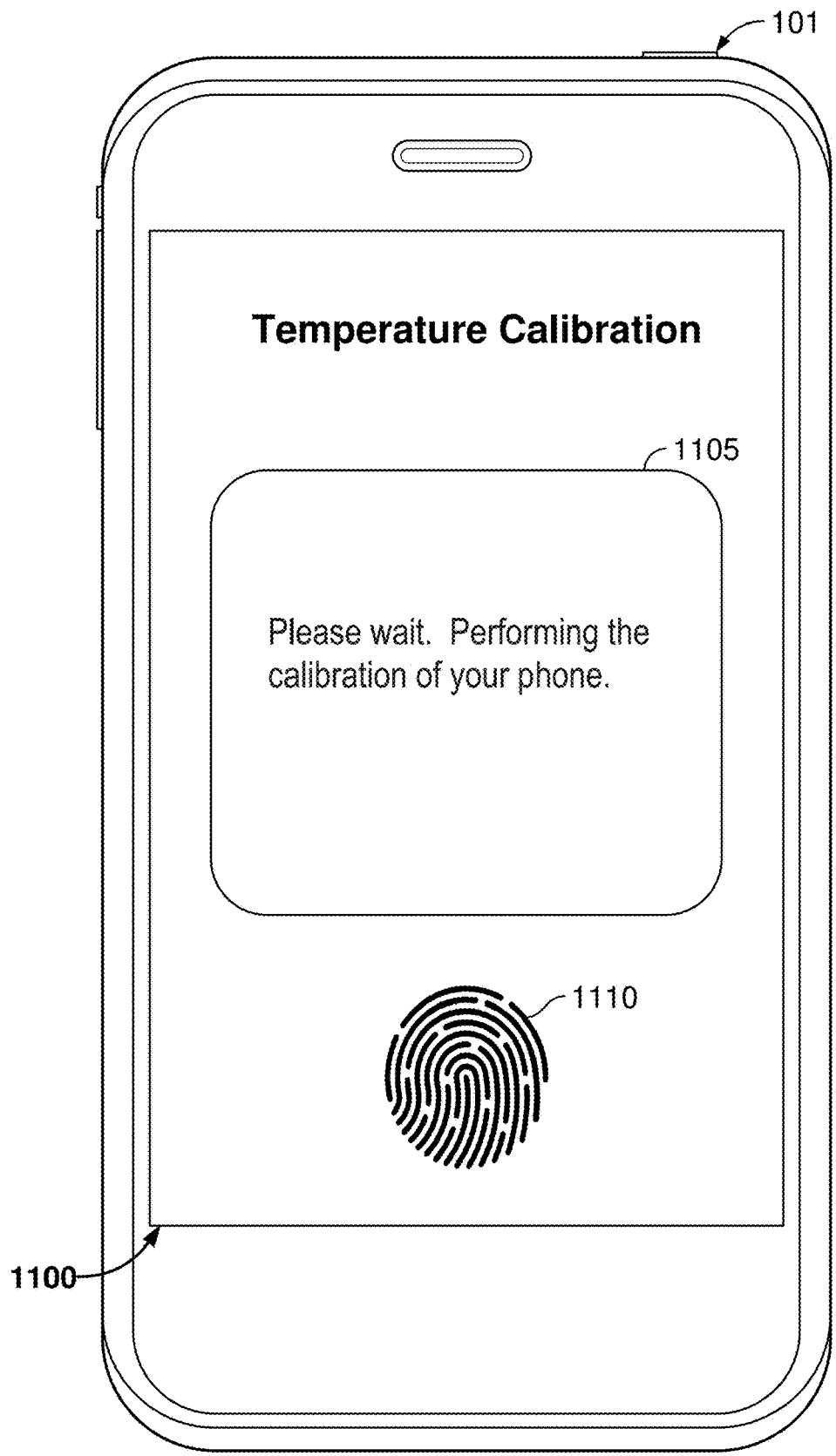

FIG. 11B shows an example of text that may be presented in the message area 1105 while the apparatus 101 is calibrating an ultrasonic sensor system. The text shown in the message area 1105 may, for example, be presented at a time during which background ultrasonic signals corresponding to reflections from a cover/air interface are obtained during a user calibration process and/or at a time during which ultrasonic signal parameters corresponding to the background ultrasonic signals are being determined. In some examples, the text shown in the message area 1105 may be presented at a time during which ultrasonic sensor system temperature data are being obtained during a user calibration process.

Figure 11C:
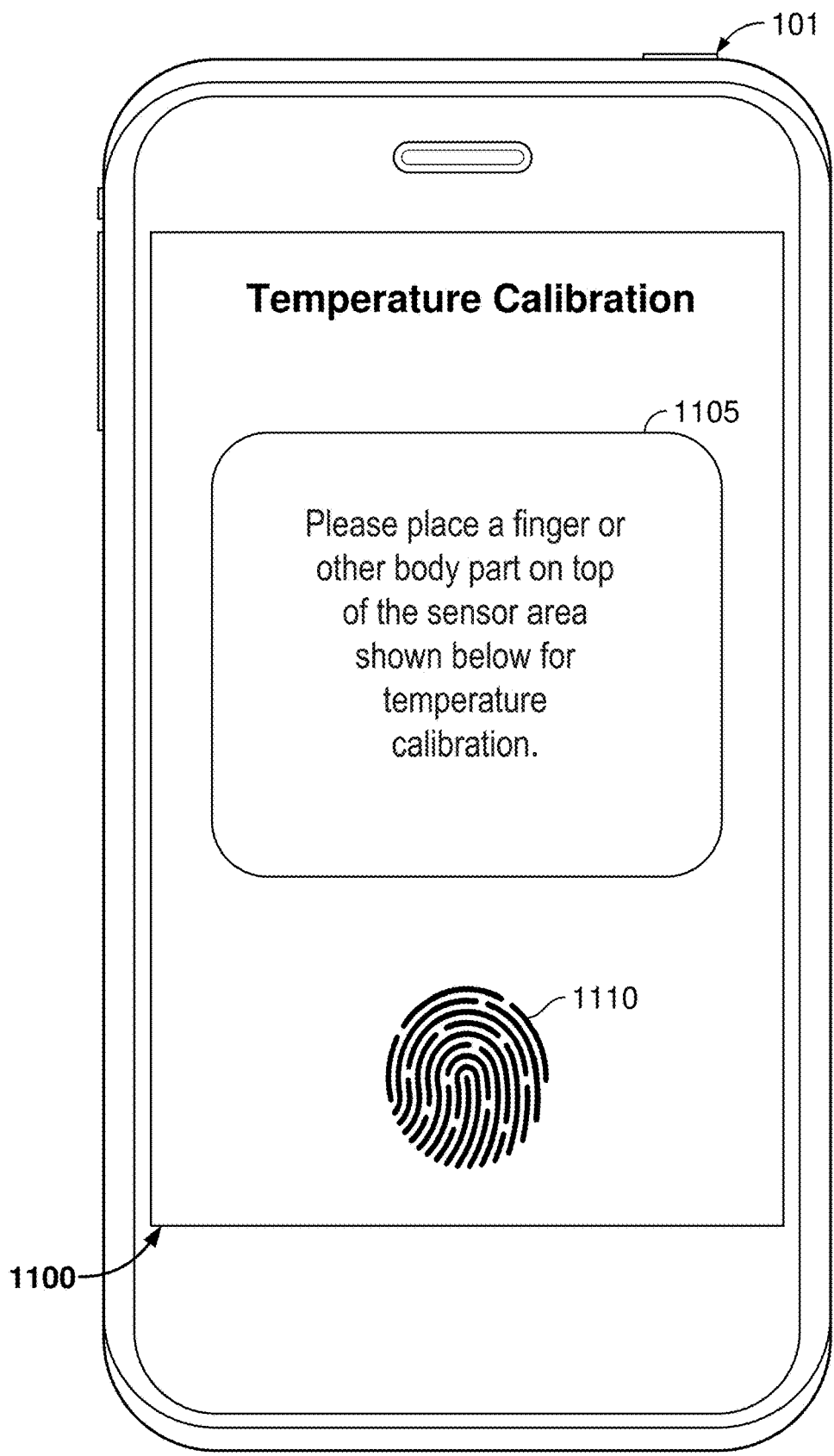

FIG. 11C shows an example of a textual prompt that may be presented in the message area 1105 prior to obtaining ultrasonic signals corresponding to a cover/target interface during a user calibration process. In this example, a user is prompted to place a finger or other body part on the ultrasonic sensor system area 1110. In some implementations, the ultrasonic sensor system area 1110 may be larger than that indicated in FIG. 11C. After the user places the body part on the ultrasonic sensor system area 1110, in some examples the ultrasonic signals corresponding to a cover/target interface (and, in some implementations, ultrasonic signals corresponding to within body part) may be acquired. According to some such examples, these ultrasonic signals may be A-line signals received by the ultrasonic sensor system electrode.

Figure 11D:
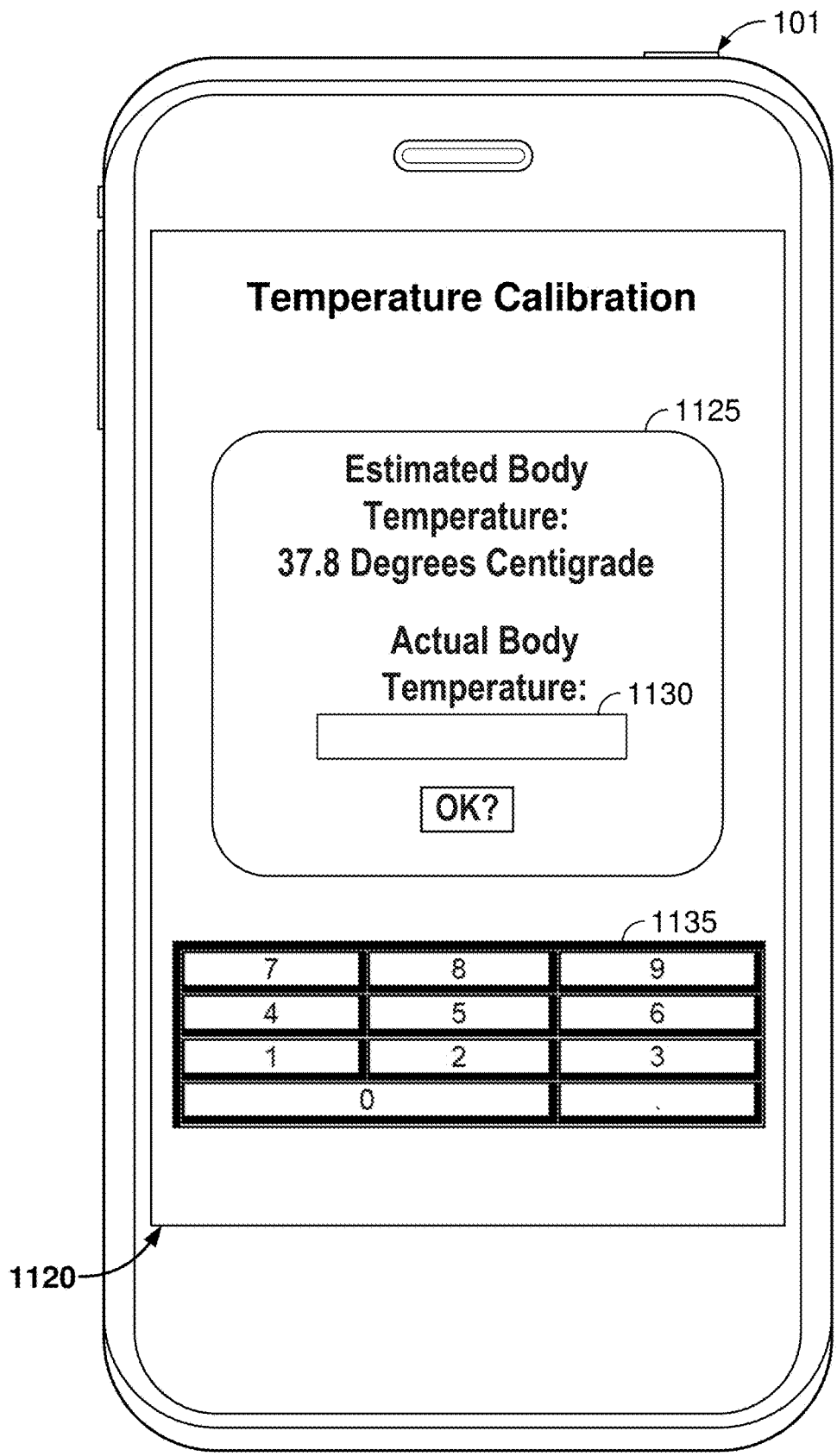

FIG. 11D shows an example of text that may be presented in a message area 1125 after the control system has estimated the user's temperature during a user calibration process. In this example, the user's estimated body temperature is presented in the message area 1125. According to this example, the message area 1125 also includes a textual prompt for the user to enter the user's actual body temperature, e.g., as measured by a thermometer, in the window 1130. In this implementation, the GUI 1120 includes a virtual keypad 1135 with which the user may interact in order to enter the user's temperature in the window 1130. The temperature estimation process may, in some implementations, be recalibrated according to user input regarding the user's actual body temperature. The results of the user calibration process may be stored in a memory for subsequent use.

As noted elsewhere herein, according to some examples the ultrasonic sensor system may include a piezoelectric layer, an electrode proximate a first side of the piezoelectric layer and an array of ultrasonic sensor pixels proximate a second side of the piezoelectric layer. The ultrasonic signals that are used to estimate a person's temperature may, in some such examples, be received via the electrode. In some implementations, a control system may be configured to perform an authentication process that is based, at least in part, on ultrasonic signals received via the array of ultrasonic sensor pixels.

In some examples, the control system 106 of FIG. 1 or FIG. 2 may be configured to receive, from the ultrasonic sensor system 102, signals corresponding to reflections of ultrasonic waves from a surface of a portion of a target object, such as a finger, that is on an outer surface of the cover 108. In some examples, the control system 106 may be configured to obtain fingerprint data based on portions of the reflected ultrasonic waves that are received within a time interval corresponding with fingerprints. The time interval may, for example, be measured relative to a time at which ultrasonic waves corresponding to the reflected ultrasonic waves are transmitted. Obtaining the fingerprint data may, for example, involve extracting, via the control system 106, fingerprint features from the first signals. According to some examples, the fingerprint features may include fingerprint minutiae, keypoints and/or sweat pores. In some examples, the fingerprint features may include ridge ending information, ridge bifurcation information, short ridge information, ridge flow information, island information, spur information, delta information, core information, etc.

In some examples, the control system 106 may be configured to perform an authentication process that is based, at least in part, on the fingerprint features. According to some examples, the control system 106 may be configured to compare the fingerprint features with previously-obtained features (e.g., obtained during a user registration or enrollment process) of a target object, such as a finger.

According to some implementations, a user calibration process may continue, at least intermittently, during an authentication process. According to some such examples, background ultrasonic image data (e.g., for a plurality of modes), as well as finger ultrasonic image data (e.g., for a plurality of modes) may be captured during an authentication process and used to update user calibration data in a memory that was previously stored during a prior user calibration process.

In some implementations, the control system 106 may be configured to extract sub-epidermal features from ultrasonic signals. In some such implementations, the sub-epidermal features may include sub-epidermal layer information corresponding to reflections received within a time interval corresponding with a sub-epidermal region. According to some implementations, a subsequent authentication process may involve comparing previously-obtained sub-epidermal features (e.g., obtained during a user registration or enrollment process) with currently-obtained sub-epidermal features.

The sub-epidermal features may, for example, include dermis layer information corresponding to reflections corresponding to the third ultrasonic signals, or to other ultrasonic signals. The dermis layer information may have been obtained within a time interval corresponding with a dermis layer. The subsequent authentication process may be based, at least in part, on the dermis layer information. Alternatively, or additionally, the sub-epidermal features may include information regarding other sub-epidermal layers, such as the papillary layer, the reticular layer, the subcutis, etc., and any blood vessels, lymph vessels, sweat glands, hair follicles, hair papilla, fat lobules, etc., that may be present within such tissue layers.

In some examples, the control system 106 may be configured for controlling access to the apparatus 101, or to another device, based at least in part on the authentication process. For example, in some implementations a mobile device (such as a cell phone) may include the apparatus 101. In some such examples, the control system 106 may be configured for controlling access to the mobile device based, at least in part, on the subsequent authentication process.

In some implementations an Internet of things (IoT) device may include the apparatus 101. For example, in some such implementations a device intended for use in a home, such as a remote control device (such as a remote control device for a smart television), a stove, an oven, a refrigerator, a stove, a coffee maker, an alarm system, a door lock, a mail/parcel box lock, a thermostat, etc., may include the apparatus 101. In some such examples, the control system may be configured for controlling access to the IoT device based, at least in part, on the authentication process.

In alternative implementations, an automobile (including but not limited to a partially or fully autonomous automobile), a partially or fully autonomous delivery vehicle, a drone, or another device typically used outside of the home may include one or more instances of the apparatus 101. In some such examples, the control system may be configured for controlling access to the vehicle, the drone, etc., based at least in part on the subsequent authentication process.

In some examples, including but not limited to many IoT implementations, there may be a metal, plastic, ceramic or polymer layer between an outer surface of the apparatus 101, or an outer surface of a device that includes the apparatus 101. In such implementations, the acoustic waves transmitted towards, and reflected from, a finger or other target may need to pass through the metal, plastic, ceramic or polymer layer. Ultrasound and other acoustic waves can be successfully transmitted through e.g., a metal layer, whereas some other types of waves (e.g., light waves) cannot. Similarly, ultrasound and other acoustic waves can be successfully transmitted through an optically opaque plastic, ceramic or polymer layer, whereas some other types of waves, such as light waves, cannot. This feature is another potential advantage of some disclosed implementations, as compared to devices that rely upon optical or capacitive fingerprint sensors.

According to some examples, the apparatus may be configured to perform a liveness detection process or another type of spoof detection process. In some instances, spoofing may involve using a finger-like object that includes silicone rubber, polyvinyl acetate (white glue), gelatin, glycerin, etc., with a fingerprint pattern of a rightful user formed on an outside surface. In some cases, a hacker may form a fingerprint pattern of a rightful user on a sleeve or partial sleeve that can be slipped over or on the hacker's finger. In some implementations, the spoof detection process may be based, at least in part, on a sleeve detection process and/or on ultrasonic signals corresponding to sub-epidermal features. Some such liveness determinations may involve obtaining first sub-epidermal features from first ultrasonic image data at a first time and obtaining second sub-epidermal features from second ultrasonic image data at a second time. Some examples may involve making a liveness determination based on a change between the first sub-epidermal features and the second sub-epidermal features. This type of temporal change may, for example, correspond with the flow of blood within a finger.

Figure 12:
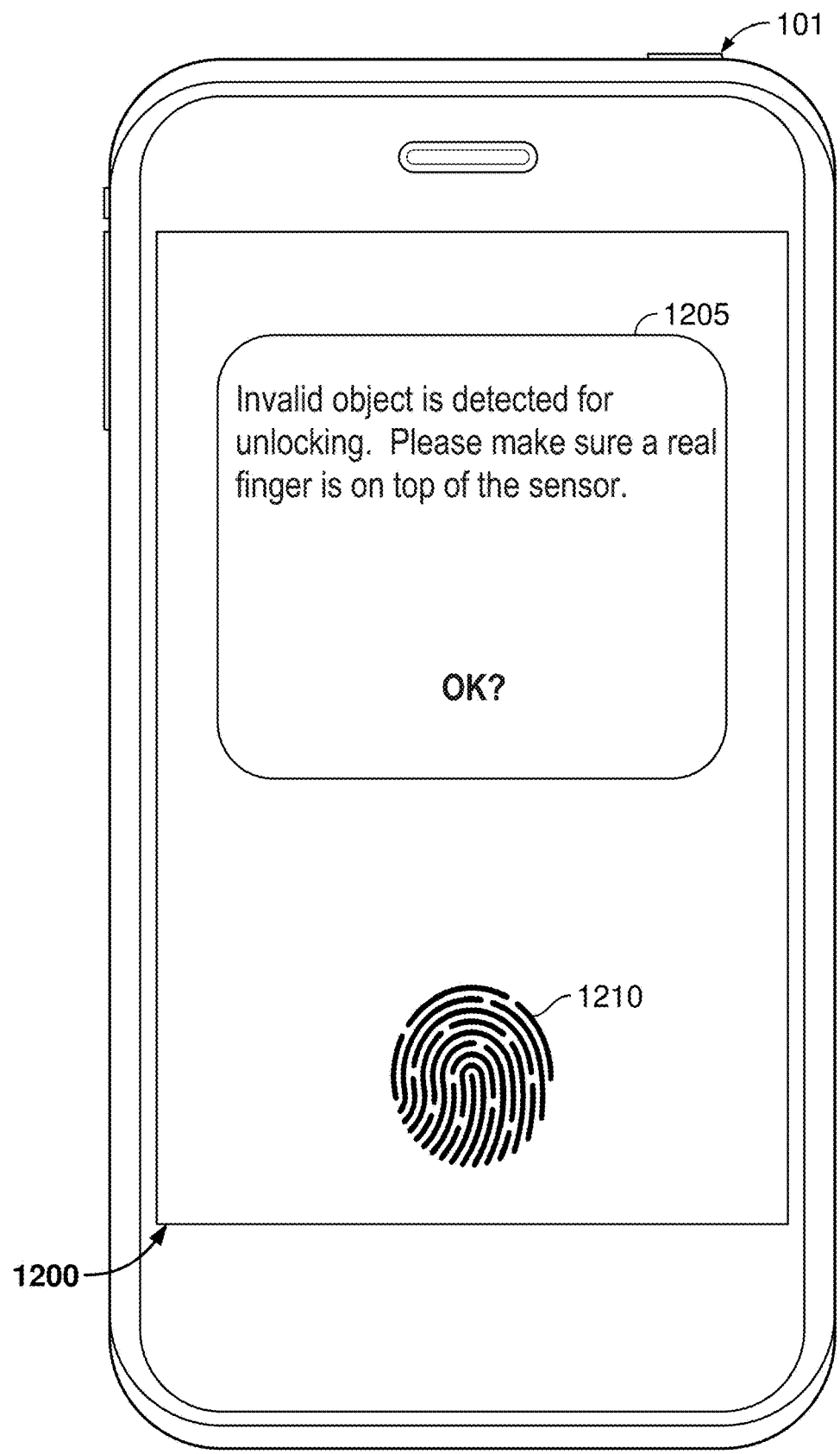
FIG. 12 shows another example of a GUI that may be presented in some implementations.

FIG. 12 shows another example of a GUI that may be presented in some implementations. In this example, the GUI 1200 is being presented in the context of a fingerprint authentication process. In some instances, the GUI 1200 may be presented after an end-user fingerprint registration process. In this example, a control system of the apparatus 101 has determined that an object in contact with the ultrasonic sensor system area 1210 is not a finger. Therefore, the control system is controlling the display to present the GUI 1200, including a message area 1205 prompting a user to ensure that an actual finger is on the ultrasonic sensor system area 1210 so that the apparatus 101 can perform the fingerprint authentication process.

Figure 13:
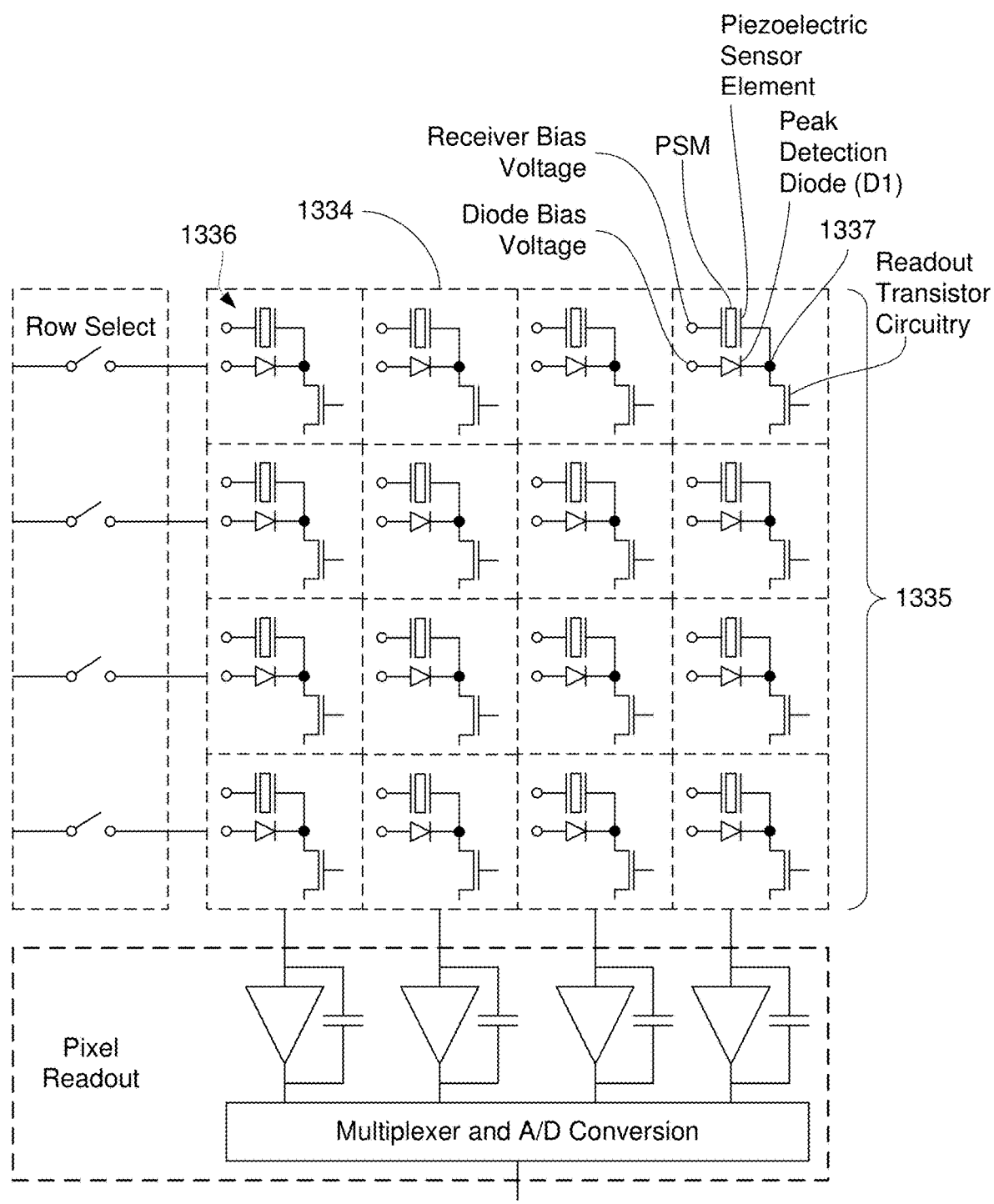
FIG. 13 representationally depicts aspects of a 4×4 pixel array of sensor pixels for an ultrasonic sensor system.

FIG. 13 representationally depicts aspects of a 4×4 pixel array of sensor pixels for an ultrasonic sensor system. Each pixel 1334 may be, for example, associated with a local region of piezoelectric sensor material (PSM), a peak detection diode (D1) and a readout transistor (M3); many or all of these elements may be formed on or in a substrate to form the pixel circuit 1336. In practice, the local region of piezoelectric sensor material of each pixel 1334 may transduce received ultrasonic energy into electrical charges. The peak detection diode D1 may register the maximum amount of charge detected by the local region of piezoelectric sensor material PSM. Each row of the pixel array 1335 may then be scanned, e.g., through a row select mechanism, a gate driver, or a shift register, and the readout transistor M3 for each column may be triggered to allow the magnitude of the peak charge for each pixel 1334 to be read by additional circuitry, e.g., a multiplexer and an A/D converter. The pixel circuit 1336 may include one or more TFTs to allow gating, addressing, and resetting of the pixel 1334.

Each pixel circuit 1336 may provide information about a small portion of the object detected by the ultrasonic sensor system. While, for convenience of illustration, the example shown in FIG. 13 is of a relatively coarse resolution, ultrasonic sensors having a resolution on the order of 500 pixels per inch or higher may be configured with an appropriately scaled structure. The detection area of the ultrasonic sensor system may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the target object.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

The invention claimed is:

1. An apparatus, comprising:
   an ultrasonic sensor system including a piezoelectric layer, an ultrasonic sensor system electrode proximate a first side of the piezoelectric layer and an array of ultrasonic sensor pixels proximate a second side of the piezoelectric layer;
   a temperature sensor configured to determine an ultrasonic sensor system temperature;
   a cover; and
   a control system, at least part of which is coupled to the ultrasonic sensor system, the control system configured to:
      receive ultrasonic sensor system temperature data from the temperature sensor, the ultrasonic sensor system temperature data indicating the ultrasonic sensor system temperature;
      acquire first ultrasonic signals via the ultrasonic sensor system, the first ultrasonic signals received by the ultrasonic sensor system electrode and corresponding to reflections from a cover/air interface;
      determine one or more first ultrasonic signal parameters of the first ultrasonic signals;
      acquire second ultrasonic signals from a target proximate the cover via the ultrasonic sensor system, the second ultrasonic signals received by the ultrasonic sensor system electrode and corresponding to reflections from a cover/target interface;
      determine one or more second ultrasonic signal parameters of the second ultrasonic signals; and
      estimate, based at least in part on the one or more first ultrasonic signal parameters, the one or more second ultrasonic signal parameters, and the ultrasonic sensor system temperature, a target object temperature of the target object.

2. The apparatus of claim 1, further comprising a memory, wherein the control system is further configured to retrieve previously-acquired ultrasonic signal parameter data and previously-acquired temperature data from the memory and to estimate the target object temperature based, at least in part, on the previously-acquired ultrasonic signal parameter data and the previously-acquired temperature data.

3. The apparatus of claim 2, wherein the target object is a body part of a user of the apparatus and wherein the previously-acquired ultrasonic signal parameter data and the previously-acquired temperature data were previously acquired from the user and via the control system during a user calibration stage.

4. The apparatus of claim 3, further comprising a user interface system, wherein the control system is further configured to control the user interface system to provide one or more user prompts.

5. The apparatus of claim 4, wherein the user interface system includes a display stack.

6. The apparatus of claim 5, wherein the cover comprises a cover glass and wherein at least a portion of the display stack resides between the cover glass and the ultrasonic sensor system.

7. The apparatus of claim 5, wherein the control system is further configured for controlling the display stack to present a graphical user interface that indicates an ultrasonic sensor system area.

8. The apparatus of claim 7, wherein the control system is configured for controlling the display stack to present text prompting the user to ensure that there is no object on or proximate the ultrasonic sensor system area prior to acquiring ultrasonic signals corresponding to reflections from the cover/air interface during the user calibration stage, prior to acquiring the first ultrasonic signals, or both during the user calibration stage and prior to acquiring the first ultrasonic signals.

9. The apparatus of claim 7, wherein the control system is configured for controlling the display stack to present text prompting the user to position the body part on the ultrasonic sensor system area prior to acquiring ultrasonic signals corresponding to reflections from a cover/body part interface during the user calibration stage, prior to acquiring the second ultrasonic signals, or both during the user calibration stage and prior to acquiring the second ultrasonic signals.

10. The apparatus of claim 5, wherein the control system is further configured for controlling the display stack to present a graphical user interface that indicates an estimated body temperature of the user.

11. The apparatus of claim 2, wherein the previously-acquired ultrasonic signal parameter data and the previously-acquired temperature data were not previously acquired from a body part of a user as the target object.

12. The apparatus of claim 11, wherein the previously-acquired ultrasonic signal parameter data and the previously-acquired temperature data were acquired from a plurality of persons.

13. The apparatus of claim 11, wherein the previously-acquired ultrasonic signal parameter data and the previously-acquired temperature data were acquired via a plurality of devices.

14. The apparatus of claim 1, wherein the one or more first ultrasonic signal parameters and the one or more second ultrasonic signal parameters include at least one parameter selected from the group consisting of frequency, amplitude, phase and decay coefficient.

15. The apparatus of claim 1, wherein acquiring the first ultrasonic signals and the second ultrasonic signals involves controlling the ultrasonic sensor system to transmit ultrasonic waves according to each of a plurality of modes, each of the modes corresponding with a different combination of ultrasonic sensor system parameters.

16. The apparatus of claim 1, wherein the control system is configured to perform an authentication process that is based, at least in part, on ultrasonic signals received via the array of ultrasonic sensor pixels.

17. The apparatus of claim 1, wherein the control system is configured to cause the piezoelectric layer to transmit ultrasonic waves by applying a voltage to the ultrasonic sensor system electrode.

18. The apparatus of claim 1, wherein the cover is optically opaque.

19. The apparatus of claim 1, wherein the second ultrasonic signals also correspond to reflections from within the target object.

20. The apparatus of claim 1, wherein the apparatus is integrated into a mobile device.

21. An apparatus, comprising:
an ultrasonic sensor system including a piezoelectric layer, an ultrasonic sensor system electrode proximate a first side of the piezoelectric layer and an array of ultrasonic sensor pixels proximate a second side of the piezoelectric layer;
a temperature sensor configured to determine an ultrasonic sensor system temperature;
a cover; and
control means for:
 receiving ultrasonic sensor system temperature data from the temperature sensor, the ultrasonic sensor system temperature data indicating the ultrasonic sensor system temperature;
 acquiring first ultrasonic signals via the ultrasonic sensor system, the first ultrasonic signals received by the ultrasonic sensor system electrode and corresponding to reflections from a cover/air interface;
 determining one or more first ultrasonic signal parameters of the first ultrasonic signals;
 acquiring second ultrasonic signals from a target proximate the cover via the ultrasonic sensor system, the second ultrasonic signals received by the ultrasonic sensor system electrode and corresponding to reflections from a cover/target interface;
 determining one or more second ultrasonic signal parameters of the second ultrasonic signals; and
 estimating, based at least in part on the one or more first ultrasonic signal parameters, the one or more second ultrasonic signal parameters, and the ultrasonic sensor system temperature, a target object temperature of the target object.

22. The apparatus of claim 21, further comprising a memory, wherein the control means includes means for:
retrieving previously-acquired ultrasonic signal parameter data and previously-acquired temperature data from the memory; and
estimating the target object temperature based, at least in part, on the previously-acquired ultrasonic signal parameter data and the previously-acquired temperature data.

23. The apparatus of claim 22, wherein the target object is a body part of a user of the apparatus and wherein the previously-acquired ultrasonic signal parameter data and the previously-acquired temperature data were previously acquired from the user and via the control means during a user calibration stage.

24. The apparatus of claim 21, further comprising a display, wherein the target object is a body part of a user of the apparatus and wherein the control means includes means for controlling the display to present a graphical user interface that indicates an estimated body temperature of the user.

25. A method, comprising:
receiving ultrasonic sensor system temperature data from a temperature sensor configured to determine an ultrasonic sensor system temperature of an ultrasonic sensor system, the ultrasonic sensor system temperature data indicating the ultrasonic sensor system temperature;
acquiring first ultrasonic signals via the ultrasonic sensor system, the first ultrasonic signals corresponding to reflections from a cover/air interface, the cover/air interface being an interface between air and a cover of an apparatus that includes the ultrasonic sensor system;
determining one or more first ultrasonic signal parameters of the first ultrasonic signals;
acquiring second ultrasonic signals from a target proximate the cover via the ultrasonic sensor system, the second ultrasonic signals received by an ultrasonic sensor system electrode and corresponding to reflections from a cover/target interface;
determining one or more second ultrasonic signal parameters of the second ultrasonic signals; and
estimating, based at least in part on the one or more first ultrasonic signal parameters, the one or more second ultrasonic signal parameters, and the ultrasonic sensor system temperature, a target object temperature of the target object.

26. The method of claim 25, further comprising:
retrieving previously-acquired ultrasonic signal parameter data and previously-acquired temperature data from a memory; and
estimating the target object temperature based, at least in part, on the previously-acquired ultrasonic signal parameter data and the previously-acquired temperature data.

27. The method of claim 26, wherein the target object is a body part of a user of the apparatus and wherein the previously-acquired ultrasonic signal parameter data and the previously-acquired temperature data were previously acquired from the user during a user calibration stage.

28. The method of claim 25, wherein the ultrasonic sensor system includes a piezoelectric layer, the ultrasonic sensor system electrode proximate a first side of the piezoelectric layer and an array of ultrasonic sensor pixels proximate a second side of the piezoelectric layer, and wherein the first ultrasonic signals are received by the ultrasonic sensor system electrode.

29. The method of claim 28, further comprising performing an authentication process that is based, at least in part, on ultrasonic signals received via the array of ultrasonic sensor pixels.

30. The method of claim 28, further comprising causing the piezoelectric layer to transmit ultrasonic waves by applying a voltage to the ultrasonic sensor system electrode.

31. The method of claim 25, wherein the one or more first ultrasonic signal parameters and the one or more second ultrasonic signal parameters include at least one parameter selected from the group consisting of frequency, amplitude, phase and decay coefficient.

32. The method of claim 25, wherein acquiring the first ultrasonic signals and the second ultrasonic signals involves controlling the ultrasonic sensor system to transmit ultrasonic waves according to each of a plurality of modes, each of the modes corresponding with a different combination of ultrasonic sensor system parameters.

33. The method of claim 25, further comprising controlling a display to present a graphical user interface that indicates an estimated target object temperature.

34. One or more non-transitory media having software stored thereon, the software including instructions for performing a method, the method comprising:
receiving ultrasonic sensor system temperature data from a temperature sensor configured to determine an ultrasonic sensor system temperature of an ultrasonic sensor system, the ultrasonic sensor system temperature data indicating the ultrasonic sensor system temperature;
acquiring first ultrasonic signals via the ultrasonic sensor system, the first ultrasonic signals corresponding to reflections from a cover/air interface, the cover/air interface being an interface between air and a cover of an apparatus that includes the ultrasonic sensor system;
determining one or more first ultrasonic signal parameters of the first ultrasonic signals;

acquiring second ultrasonic signals from a target proximate the cover via the ultrasonic sensor system, the second ultrasonic signals received by an ultrasonic sensor system electrode and corresponding to reflections from a cover/target interface;

determining one or more second ultrasonic signal parameters of the second ultrasonic signals; and estimating, based at least in part on the one or more first ultrasonic signal parameters, the one or more second ultrasonic signal parameters, and the ultrasonic sensor system temperature, a target object temperature of the target object.

35. The one or more non-transitory media of claim 34, wherein the method further comprises:

retrieving previously-acquired ultrasonic signal parameter data and previously-acquired temperature data from a memory; and estimating the target object temperature based, at least in part, on the previously-acquired ultrasonic signal parameter data and the previously-acquired temperature data.

36. The one or more non-transitory media of 35, wherein the target object is a body part of a user of the apparatus and wherein the previously-acquired ultrasonic signal parameter data and the previously-acquired temperature data were previously acquired from the user during a user calibration stage.

37. The one or more non-transitory media of claim 34, wherein the ultrasonic sensor system includes a piezoelectric layer, an ultrasonic sensor system electrode proximate a first side of the piezoelectric layer and an array of ultrasonic sensor pixels proximate a second side of the piezoelectric layer, and wherein the first ultrasonic signals are received by the ultrasonic sensor system electrode.

38. The one or more non-transitory media of claim 34, wherein the method further comprises controlling a display to present a graphical user interface that indicates an estimated target object temperature.

\* \* \* \* \*